(12) United States Patent
Weerasooriya et al.

(10) Patent No.: US 9,266,821 B2
(45) Date of Patent: Feb. 23, 2016

(54) PROCESS FOR MAKING FATTY AMIDES

(75) Inventors: Upali Weerasooriya, Austin, TX (US);
John Boorem, Kansas City, KS (US);
Brian Hodle, Kansas City, KS (US);
Aaron Boorem, Kansas City, KS (US);
Peter Radford, Shawnee, KS (US);
Howard Stevenson, Overland Park, KS (US); G. Gerald Barr, Mound City, KS (US)

(73) Assignee: HARCROS CHEMICALS INC., Kansas City, KS (US)

( * ) Notice: Subject to any disclaimer, the term of this patent is extended or adjusted under 35 U.S.C. 154(b) by 1296 days.

(21) Appl. No.: 12/580,467

(22) Filed: Oct. 16, 2009

(65) Prior Publication Data
US 2011/0092715 A1  Apr. 21, 2011

(51) Int. Cl.
*C07D 233/04* (2006.01)
*C07C 231/02* (2006.01)
*C07C 233/36* (2006.01)

(52) U.S. Cl.
CPC ............ *C07C 231/02* (2013.01); *C07D 233/04* (2013.01)

(58) Field of Classification Search
None
See application file for complete search history.

(56) References Cited

U.S. PATENT DOCUMENTS

| | | |
|---|---|---|
| 2,970,160 A | 1/1961 | Walker |
| 2,985,662 A | 5/1961 | Johnson et al. |
| 3,641,072 A | 2/1972 | Distler et al. |
| 3,950,417 A | 4/1976 | Verdicchio et al. |
| 4,231,903 A | 11/1980 | Lindemann et al. |
| 4,233,192 A | 11/1980 | Lindemann et al. |
| 4,261,911 A | 4/1981 | Lindemann et al. |
| 4,265,782 A | 5/1981 | Armstrong et al. |
| 4,754,075 A | 6/1988 | Knopf et al. |
| 4,775,653 A | 10/1988 | Leach et al. |
| 4,800,077 A | 1/1989 | O'Lenick, Jr. et al. |
| 4,820,673 A | 4/1989 | Knopf et al. |
| 4,835,321 A | 5/1989 | Leach et al. |
| 4,886,917 A | 12/1989 | Knopf et al. |
| 5,015,412 A | 5/1991 | Zeman |
| 5,220,046 A | 6/1993 | Leach et al. |
| 5,220,077 A | 6/1993 | Sandoval et al. |
| 5,386,045 A | 1/1995 | Weerasooriya et al. |
| 5,607,980 A | 3/1997 | McAtee et al. |
| 5,627,121 A | 5/1997 | Lin et al. |
| 5,658,749 A | 8/1997 | Thornton |
| 6,147,246 A | 11/2000 | Weerasooriya et al. |
| 6,525,016 B2 | 2/2003 | Liew |
| 6,620,904 B2 | 9/2003 | Lemke |
| 7,033,989 B2 | 4/2006 | Keck et al. |
| 7,119,236 B2 | 10/2006 | Weerasooriya et al. |
| 2007/0010680 A1 | 1/2007 | Yajima et al. |
| 2007/0060770 A1 | 3/2007 | Matheson et al. |

FOREIGN PATENT DOCUMENTS

EP  1 672 056  6/2006
WO  WO 2006/024898  3/2006

*Primary Examiner* — Alicia L Otton
(74) *Attorney, Agent, or Firm* — Stinson Leonard Street LLP

(57) ABSTRACT

A process for reacting, in the presence of a particular calcium containing catalyst, an amine having an active hydrogen and one or more of a fatty acid ester or a fatty acid.

59 Claims, No Drawings

PROCESS FOR MAKING FATTY AMIDES

CROSS-REFERENCE TO RELATED APPLICATIONS

Not applicable.

STATEMENT REGARDING FEDERALLY SPONSORED RESEARCH OR DEVELOPMENT

Not applicable.

BACKGROUND OF THE INVENTION

1. Field of the Invention

The present invention is directed to novel methods of preparing fatty amides and their derivatives, such as betaines and their phosphorous-containing or sulfur-containing analogues. Among other things, the products are useful as surface active agents.

2. Description of Related Art

Fatty amide production generally involves the reaction of a fatty acid source, such as a triglyceride, with an amine. Similarly, fatty amidoamine production generally involves the reaction of N,N-dimethylaminopropylamine ("DMAPA") with a triglyceride, such as coconut oil, using an alkaline catalyst such as sodium methylate at elevated temperatures. This results in a viscous, highly colored blend of the corresponding amidoamine and glycerol. The present invention is directed to a method for synthesizing such fatty amidoamines (and products formed from such amidoamines) and other amides using a calcium-containing catalyst which results in a more desirable overall product composition.

BRIEF SUMMARY OF THE INVENTION

The present invention is directed to a process of reacting, in the presence of a calcium-containing catalyst, an amine having an active hydrogen and one or more of a fatty acid ester or a fatty acid. The resulting composition comprises the desired fatty amide, but the overall product composition exhibits superior physical properties, such as viscosity, clarity, and ease of production compared to that using traditional alkaline catalysts. The preferred catalyst is generally described in U.S. Pat. No. 7,119,236, and the most preferred catalyst is referred to herein as the "U-Cat."

In one aspect, the fatty amides formed using the catalyst as described herein are fatty amidoamines useful in the preparation of a wide variety of amphoteric compounds, including but not limited to betaines, sulfobetaines (sultaines), sulfitobetaines, sulfatobetaines, phosphinate betaines, phosphonate betaines, phosphitobetaines, phosphatobetaines, and the like. The beneficial superior physical properties of the compositions containing the amidoamines likely extend to the downstream product compositions containing these amphoteric compounds. In one aspect, for example, the amphoteric compounds exist as a stable concentrated aqueous composition having solid content of at least 30 wt %, preferably 35 wt %, and most preferably at least 40 wt % such that the compositions have excellent properties at these concentrations with respect to low viscosity and low gel point. In addition, the compositions of the amphoteric compounds generally have low free fatty acid contents (for example, 1 wt % for the U-Cat catalyzed compared to 4 wt % for the sodium methylate catalyzed reactions).

In another aspect, the fatty amidoamines may also be readily converted to the corresponding cyclic derivatives, such as imidazolines, or the corresponding amidoamine oxides. The fatty amidoamines and imidazolines may also be quaternized.

Additional aspects of the invention, together with the advantages and novel features appurtenant thereto, will be set forth in part in the description which follows, and in part will become apparent to those skilled in the art upon examination of the following, or may be learned from the practice of the invention. The objects and advantages of the invention may be realized and attained by means of the instrumentalities and combinations particularly pointed out in the appended claims.

DETAILED DESCRIPTION OF PREFERRED EMBODIMENT

The present invention is directed to a process of reacting, in the presence of a calcium-containing catalyst, an amine having an active hydrogen and one or more of a fatty acid ester or a fatty acid. The resulting composition comprises the desired fatty amide, but the overall product composition exhibits superior physical properties, such as viscosity, clarity, and ease of production compared to that using traditional alkaline catalysts.

The preferred calcium-containing catalysts are those which have previously been employed for alkoxylation processes. For example, Smith et al., WO 2006/025898, which is incorporated by reference, generally describes an alkoxylation catalyst comprising a calcium-containing compound modified by the addition of a acid, preferably a strong acid, generally referred to herein as "Catalyst Z". Carboxylic acids or ether components are optionally added to the catalyst composition. More specifically, in one aspect of the invention, Catalyst Z is formed by a method comprising the steps of: a) combining an alkaline-earth compound (preferably a compound of calcium) with a carboxylic acid to form a first mixture; b) adding a strong mineral acid, such as sulfuric acid, to said first mixture to form a second mixture; and c) mixing the second mixture to a uniform appearance. Additionally, optional materials such as solvents, carriers, fluidizers, etc. may be present at any stage of the process for producing the catalyst. Polyalkylene glycols and polyoxyalkylated alcohols, including alkyl-end-capped glycol ethers, are preferable, including those sold by Huntsman, LLC of Houston Tex. under the tradename POGOL®MP-116 glycol ether. In another aspect of the invention. Catalyst Z is formed by a method comprising the steps of: a) combining an alkaline-earth compound (preferably a compound of calcium) with one or more additional materials selected from the group consisting of: a carboxylic acid, a polyalkylene glycol having a molecular weight between about 100 and 1000, an $C_1$-$C_{10}$ alkyl-capped polyalkylene glycol having molecular weight between about 100 and 1000, and mixtures including any of the foregoing, to form a first mixture; b) combining said first mixture with at least one ionic chemical species selected from the group consisting of: sulfuric acid, an organic sulfonic acid, an organic sulfonate, a sulfate, a bisulfate, a sulfite, a bisulfite, any $C_1$-$C_{12}$ carboxylic acid, or any $C_1$-$C_{12}$ carboxylate so as to form a second mixture; and c) mixing said second mixture to a uniform appearance, to provide a finished catalyst. Leach, U.S. Pat. No. 4,775,653 and Sandoval et al., U.S. Pat. No. 5,220,077, which are both incorporated by reference, generally describe an alkoxylation catalyst comprising a calcium-containing compound, an alkoxylated alcohol as a dispersing medium, an inorganic acid, and a metal alkoxide, such as aluminum alkoxide or titanium alkoxide (generally referred to herein as "Catalyst A"). Knopf et al., U.S. Pat. Nos.

4,754,075 and 4,820,673, which are incorporated by reference, describe a catalyst comprising a calcium compound provided in a solvent medium (ethylene glycol, propylene glycol, diethylene glycol, glycerol, butanediols, propane diol, and the like) modified by a strong inorganic acid, like sulfuric acid or phosphoric acid (generally referred to herein as "Catalyst B"). Lin et al., U.S. Pat. No. 5,627,121, which is incorporated by reference, describes an alkoxylation catalyst comprising a calcium-containing compound at least partially dispersed in an alkoxylated alcohol mixture, wherein a carboxylic acid is added to produce a calcium composition having titratable alkalinity, and the composition is preferably partially neutralized with an inorganic acid to produce a partially neutralized calcium-containing catalyst (generally referred to herein as "Catalyst C"). Weerasooriya et al., U.S. Pat. No. 7,119,236, which is also incorporated by reference, describes an improved alkoxylation catalyst suitable for alkoxylating compounds. The alkoxylation catalyst comprises a calcium-containing compound in a dispersing medium having a boiling point less than 160° C. with a carboxylic acid and an inorganic acid or anhydride (generally referred herein as "Catalyst D"). Combinations of such catalysts are also contemplated, such as those in Matheson et al., U.S. Patent Pub. No. 2007/0060770, which is incorporated by reference (generally referred to herein as "Catalyst Y").

The present invention is directed to a new use for such calcium-containing alkoxylation catalysts. In the present invention, these calcium-containing catalysts are used to form fatty amides by reacting an amine having an active hydrogen and one or more of a fatty acid ester or a fatty acid.

DEFINITIONS

As used herein, the term "alkyl" embraces branched or unbranched saturated hydrocarbon group of one to 26 carbon atoms, such as methyl, ethyl, n-propyl, isopropyl, n-butyl, isobutyl, t-butyl, octyl, decyl, and the like. "Lower alkyl" refers to an alkyl having one to 6 carbon atoms. The term "unsaturated alkyl" refers to alkyl groups having one or more double bonds or triple bonds.

The term "alkoxy" as used herein embraces an alkyl group which has an oxygen atom attached thereto. Representative alkoxy groups include ethoxy, propoxy, iso-propoxy, sec-propoxy, butoxy, iso-butoxy, sec-butoxy, tert-butoxy, and the like.

The term "aryl" means a carbocyclic aromatic system containing one, two, or three rings wherein such rings may be attached together in a pendant manner or may be fused. The term "fused" means that a second ring is present (i.e., attached or formed) by having two adjacent atoms in common (i.e., shared) with the first ring. The term "fused" is equivalent to the term "condensed." The term "aryl" embraces aromatic groups such as phenyl, naphthyl, tetrahydronaphthyl, indane, and biphenyl.

The term "aralkyl" embraces aryl-substituted alkyl moieties. Preferable aralkyl groups are "lower aralkyl" groups having aryl groups attached to alkyl groups having one to six carbon atoms. Examples of such groups include benzyl, diphenylmethyl, triphenylmethyl, phenylethyl, and diphenylethyl.

As used herein, the term "alcohol" embraces an alkyl group, which may be saturated or unsaturated, having one or more hydroxy (—OH) substituents. Primary, secondary, and tertiary alcohols are contemplated, such as mono-alcohols as well as polyhydroxy variants. Lower alcohols are those containing from about 1 to 4 carbon atoms. Exemplary alcohols include methanol, ethanol, 1-propanol, 2-propanol, 2-pro-pen-1-ol, 1-butanol, 2-butanol, 2-methyl-2-propanol, 1-pentanol, 2-pentanol, 3-pentanol, and 3-methyl-1-butanol.

As used herein, the term "hydroxyl" or "hydroxy" means —OH.

As used herein, the term "alkoxylated hydroxyl" refers to one or more alkoxy groups having a terminal hydroxyl end group. Thus, the term encompasses the group —O($C_tH_{2t}$)$_n$OH, wherein t and n are independently 1, 2, 3, 4, 5, or 6. Preferred alkoxylated hydroxyls are ethoxylated hydroxyls such as those according to —(OCH$_2$CH$_2$)$_n$OH wherein n is an integer from 1 to 5.

A. Preparation of the Preferred Calcium-Containing Catalyst

Preparation of the Preferred Calcium-Containing Catalyst is Described in U.S. Pat. No. 7,119,236 which is incorporated by reference in its entirety. In preparing the catalyst according to the process of the present invention, a calcium-containing compound that is at least partially dispersible in a volatile organic dispersing medium is admixed together with a carboxylic acid. The calcium/carboxylic acid mole ratio preferably ranges from about 15:1 to about 1:1. Following solubilization, an inorganic acid, anhydride, or a mixture thereof is introduced into the reaction mixture. Preferably, the inorganic acid is in an amount sufficient to neutralize at least 25% of the titratable alkalinity present in the mixture.

The calcium-containing compounds used in the present invention are ones that are at least partially dispersible or soluble in the volatile dispersing medium. Examples of specific calcium-containing compounds/compositions include one or more reaction products of calcium with various alcohols (alcoholates such as calcium alkoxides and phenoxides) as well as oxide, hydroxide, carbide, and carboxylate compounds, e.g., acetates, formates, oxalates, citrates, lactates, benzoates, laurates, and stearates. While compounds such as calcium hydride, calcium acetate, and calcium oxalate, may be used, it is preferred that the calcium-containing compound be calcium oxide, calcium hydroxide, or a mixture thereof.

The carboxylic acids useful in the present invention include any suitable compound having a —COOH moiety or precursors to —COOH moieties as in anhydrides. The carboxylic acids include aliphatic or aromatic compounds having a mono-, di-, or poly-COOH moiety. While it is preferred that the carboxylic acids be saturated, they may optionally contain other functional groups such as hydroxyl groups that do not interfere with the reaction. Most preferably, the carboxylic acids of the present invention are branched chain or linear monocarboxylic acids. In addition, the preferred carboxylic acids have from about 2 to 18 carbon atoms, most preferably between 4 to about 15 carbon atoms. Most preferred carboxylic acids are those that have good miscibility in organic solvents. Non-limiting examples of such suitable acids include octanoic acid, 2-methyl hexanoic acid, heptanoic acid, 3-methyl octanoic acid, 4-ethyl nonanoic acid, and 2-ethyl hexanoic acid.

The preferred inorganic acids and anhydrides that are useful in the process of the present invention include sulfuric acid, phosphoric acid, polyphosphoric acid, oleum, sulfur trioxide, and phosphorous pentoxide. Particularly preferred are the oxy acids such as sulfuric acid.

The preferred volatile dispersing medium of the present invention "consists essentially of" media having a boiling point less than about 160° C., even more preferably less than about 150° C., still more preferably less than about 140° C., and even more preferably less than about 120° C. The dispersing media preferably consists essentially of media having a boiling point between about 80° C. and about 160° C., and even more preferably between about 80° C. and about 120° C.

As used herein, the phrase "consisting essentially of" with respect to the volatile dispersing media of the present invention means that other components may be added to the media without materially affecting the basic and novel characteristic of the invention. That is, the volatile dispersing medium of the present invention may contain minor components having higher boiling points (above 160° C.). However, these minor components preferably comprise less than 10% by weight, even more preferably less than 5% by weight, still more preferably less than 1% by weight, and most preferably less than 0.1% by weight of the total weight of the dispersing medium.

Most preferably, the dispersing medium of the present invention "consists of" media having a boiling point less than 160° C., even more preferably less than about 150° C., still more preferably less than about 140° C., and even more preferably less than about 120° C. Most preferably, the dispersing media preferably consists essentially of media having a boiling point between about 80° C. and about 160° C., and even more preferably between about 80° C. and about 120° C. As used herein, the phrase "consisting of" excludes any ingredient that does not have a boiling point as specified.

Suitable volatile dispersing media include alcohols, esters, ethers, ketones, aldehydes, and other aliphatic and aromatic hydrocarbons having a boiling point less than 160° C., and mixtures thereof.

The preferred dispersing medium is preferably a lower straight chain or branched alcohol. Most preferably, the dispersing medium is butanol. Other suitable alcohols include, but are not limited to, methanol (65° C.), ethanol (78° C.), 1-propanol (106° C.), 2-propanol (82.5° C.), 2-methyl-2-propanol (82.4° C.), 1-butanol (117° C.), 2,3-dimethyl-1-butanol (142° C.), 3,3-dimethyl-1-butanol (143° C.), 2-diethyl-1-butanol (146° C.), 2-methyl-1-butanol (129° C.), 3-methyl-1-butanol (131° C.), 2-butanol (99.5° C.), 2-methyl-2-butanol (102° C.), 2,3-dimethyl-2-butanol (118° C.), 3,3-dimethyl-2-butanol (120° C.), 3-methyl-2-butanol (112° C.), 2-methyl-1-pentanol (148° C.), 3-methyl-1-pentanol (152° C.), 4-methyl-1-pentanol (152° C.), 2-pentanol (119° C.), 2,4-dimethyl-2-pentanol (133° C.), 2-methyl-2-pentanol (120° C.), 3-methyl-2-pentanol (134° C.), 4-methyl-2-pentanol (133° C.), 3-pentanol (116° C.), 2,4,4-trimethyl-2-pentanol (147° C.), 2,2-dimethyl-3-pentanol (135° C.), 2,3-dimethyl-3-pentanol (140° C.), 2,4-dimethyl-3-pentanol (139° C.), 3-ethyl-3-pentanol (143° C.), 3-ethyl-2-methyl-3-pentanol (159° C.), 2-methyl-3-pentanol (127° C.), 2,3,4-trimethyl-3-pentanol (157° C.), 1-pentanol (138° C.) and 1-hexanol (158° C.), 2-hexanol (138° C.), 2-methyl-2-hexanol (143° C.), 5-methyl-2-hexanol (150° C.), 3-hexanol (135° C.), and 3-methyl-3-hexanol (143° C.).

Volatile esters, such as methyl- and ethyl-esters of formic acid, acetic acid, propionic acid, butyric acid may also be useful as dispersing media. Exemplary dispersing media involving formic acid derivatives include, but are not limited to, allyl formate (83.6° C.), butyl formate (106.8° C.), isobutyl formate (98.4° C.), sec-butyl formate (97° C.), ethyl formate (54.5° C.), hexyl formate (156° C.), methyl formate (31.5° C.), pentyl formate (132° C.), isopentyl formate (124° C.), propyl formate (81.3° C.), and isopropyl formate (68° C.).

Exemplary dispersing media involving acetic acid derivatives include, but are not limited to, allyl acetate (103° C.), butyl acetate (126° C.), iso-butyl acetate (117° C.), sec-butyl acetate (112° C.), tert-butyl acetate (97° C.), ethyl acetate (77° C.), methyl acetate (57° C.), tert-amyl acetate (124° C.), isopentyl acetate (142° C.), 2-methyl-3-pentyl acetate (148° C.), 3-methyl-3-pentyl acetate (148° C.), 4-methyl-2-pentyl acetate (147° C.), pentyl acetate (139° C.), 2-pentyl acetate (130° C.), 3-pentyl acetate (132° C.), propyl acetate (101° C.), isopropyl acetate (90° C.), and 1,2,2-trimethyl propyl acetate (141° C.).

Exemplary dispersing media involving propionic acid derivatives include, but are not limited to, allyl propionate (124° C.), butyl propionate (145° C.), isobutyl propionate (136° C.), sec-butyl propionate (132° C.), ethyl propionate (99° C.), propyl propionate (122° C.), isopropyl propionate (109° C.), and methyl propionate (79.9° C.).

Exemplary dispersing media involving butyric acid derivatives include, but are not limited to, sec-butyl butyrate (151° C.), iso-butyl butyrate (157° C.), tert-butyl butyrate (145° C.), ethylbutyrate (121° C.), ethyl-2-methyl butyrate (131° C.), isopropyl-3-methyl butyrate (142° C.), ethyl isovalerate (134° C.), methyl isovalerate (116° C.), propyl isovalerate (156° C.), propyl butyrate (143° C.), and iso-propyl butyrate (130° C.).

Exemplary ethers that can be used as dispersing media in accordance with the present invention include, but are not limited to, dimethyl ether (25° C.), diethyl ether (35° C.), dimethoxy ethane (85° C.), diethoxymethane (87° C.), dibutylether (142° C.), and diisopropyl ether (68° C.).

Exemplary ketones and aldehydes useful as dispersing media in the present invention include, but are not limited to, acetaldehyde (21° C.), propionaldehyde (49° C.), butyraldehyde (75° C.), hexanal (131° C.), heptanal (153° C.), acetone (55° C.), butanone (80° C.), penantones (101-102° C.), hexanones (123-127° C.), and heptanones (145-150° C.).

The catalysts of the present invention may optionally be prepared using activators, which as those disclosed in Knopf et al., U.S. Pat. Nos. 4,754,075 and 4,886,917, as well as King, U.S. Pat. Nos. 5,114,900 and 5,120,697, all of which are incorporated by reference. In addition, aluminum alkoxide as disclosed in Leach et al. U.S. Pat. No. 4,835,321, which is incorporated by reference, may also be used to prepare the catalysts of the present invention.

In forming the catalyst according to the process of the present invention, water may be volatilized in the process. Alternatively, the dispersing media, the calcium-containing compound, the carboxylic acid, and the neutralizing acid can be reacted or combined under conditions that prevent any loss of water that is either initially present or formed during the reaction, thus forming a highly active catalyst. It is postulated that by keeping the water in the system during the reaction to form the catalyst, there is enhanced solubilization of the active calcium catalyst species that leads to the production of a more active catalyst. For example, if the reaction is conducted at elevated temperatures, super-atmospheric pressure can be used to prevent loss of water. Preferably, the reaction is conducted at elevated temperatures under total reflux to prevent loss of water.

B. Use of Catalyst: Preparation of Amidoamines and Amides

In one embodiment of the present invention, the catalyst described herein is used to form fatty amidoamines, fatty amides, and their derivatives. In general, the catalyst is reacted with (1) an amine having at least one active hydrogen and (2) a fatty acid ester, fatty acid, or combinations thereof. The reaction generally takes place under heat, typically from about 250° F. to 320° F. Equivalent amounts of the reactants are preferably employed.

In general, the amine has at least one active hydrogen. In one aspect, the amine having the one active hydrogen is a diamine, such as one according to:

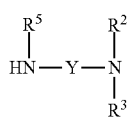

wherein $R^2$ and $R^3$ are independently selected from the group consisting of hydrogen or lower alkyl optionally substituted with one or more hydroxyls or alkoxylated hydroxyls (preferably methyl, ethyl, —CH$_2$CH$_2$OH, or —CH$_2$CH$_2$(OCH$_2$CH$_2$)$_n$OH wherein n is an integer from 1 to 5), and at least one of $R^2$ and $R^3$ is not hydrogen;

wherein $R^5$ is hydrogen or alkyl (preferably hydrogen or lower alkyl); and wherein Y is alkyl (preferably lower alkyl).

More preferably, the diamine is an N,N-dialkylaminoalkylamine, N-alkylaminoalkylamine, N,N-dialkanolaminoalkylamine, or N-alkanolaminoalkylamine. Thus, in another aspect, the diamine is one defined according to:

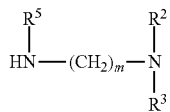

wherein $R^2$ and $R^3$ are independently selected from the group consisting of hydrogen or lower alkyl optionally substituted with one or more hydroxyls or alkoxylated hydroxyls (preferably methyl, ethyl, —CH$_2$CH$_2$OH, or —CH$_2$CH$_2$(OCH$_2$CH$_2$)$_n$OH wherein n is an integer from 1 to 5), and at least one of $R^2$ and $R^3$ is not hydrogen;

wherein $R^5$ is hydrogen or alkyl (preferably hydrogen or lower alkyl); and wherein m is 1, 2, 3, 4, 5, or 6 (preferably 2 or 3).

Still more preferably, the N,N-dialkylaminoalkylamine has three carbons in the linker, with N, —N-dimethylaminopropylamine, H$_2$N(CH$_2$)$_3$N(CH$_3$)$_2$, being most preferred.

In another aspect, the amine having the one active hydrogen is a monoamine, preferably an alkylamine, dialkylamine, dialkanolamine, or monoalkanolamine, such as one according to:

wherein $R^2$ and $R^3$ are independently selected from the group consisting of hydrogen or lower alkyl optionally substituted with one or more hydroxyls or alkoxylated hydroxyls (preferably methyl, ethyl, —CH$_2$CH$_2$OH, or —CH$_2$CH$_2$(OCH$_2$CH$_2$)$_n$OH wherein n is an integer from 1 to 5), and at least one of $R^2$ and $R^3$ is not hydrogen;

The preferred monoamines include diethanolamine (HN(CH$_2$CH$_2$OH)$_2$) and ethanolamine (H$_2$NCH$_2$CH$_2$OH).

As discussed above, the amine having the at least one active hydrogen is reacted with a fatty acid ester, fatty acid, or combinations thereof in the presence of the catalyst. The fatty acid ester is preferably a glyceride. In general, a glyceride is an ester of one or more fatty acids with glycerol (1,2,3-propanetriol). If only one position of the glycerol backbone molecule is esterified with a fatty acid, a "monoglyceride" is produced; if two positions are esterified, a "diglyceride" is produced; and if all three positions of the glycerol are esterified with fatty acid a "triglyceride" or "triacylglycerol" is produced. Most natural fats and oils are triglycerides. Thus, in one aspect, the triglyceride reactants used with the catalyst in accordance with the present invention are defined according to:

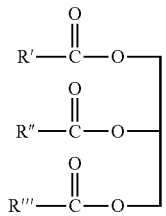

wherein R', R", and R'" are independently a saturated or unsaturated, straight or branched chain alkyl having from about 5 to about 25 carbon atoms, preferably about 9 to about 21 carbon atoms, and more preferably still from about 11 to about 17 carbon atoms and optionally substituted with one or more hydroxyls.

A phospholipid (also called a "phosphoglyceride" or "phosphatide") is a special type of glyceride. A phosphoglyceride differs from a triglyceride in having a maximum of two esterified fatty acids, while the third position of the glycerol backbone is esterified to phosphoric acid, becoming a "phosphatidic acid." In nature, phosphatidic acid is usually associated with an alcohol which contributes a strongly polar head. Two such alcohols commonly found in nature are choline and enthanolamine. A "lecithin" is a phosphatidic acid associated with the aminoalcohol, "choline," and is also known as "phosphatidylcholine." Lecithins vary in the content of the fatty acid component and can be sourced from, for example, eggs and soy. Cephalin (phosphatidylethanolamine), phosphatidylserine and phosphatidylinositol are other phosphoglycerides. Such compounds are also "glycerides" as used herein.

The preferred glycerides are triglycerides, especially those comprising C$_6$ to C$_{26}$ fatty acids, and more preferably having a chain length of at least 8, 10, 12, 14, 16, 18, 20, 22, or 24 carbons. The exemplary chain length of the fatty acid component of the glyceride ranges from about 12 to about 18 carbon atoms, and the fatty acid maybe saturated, monounsaturated, or polyunsaturated. The fatty acids may be optionally substituted with one or more hydroxyl groups. In the case of unsaturated fatty acids, both conjugated and unconjugated systems are contemplated.

Examples of saturated fatty acids include, but are not limited to C$_4$ butyric acid (butanoic acid), C$_5$ valeric acid (pentanoic acid), C$_6$ caproic acid (hexanoic acid), 2-ethyl hexanoic acid, C$_7$ enanthic acid (heptanoic acid), C$_8$ caprylic acid (octanoic acid), iso-octanoic acid, C$_9$ pelargonic acid (nonanoic acid), C$_{10}$ capric acid (decanoic acid), C$_{11}$ hendecanoic acid, C$_{12}$ lauric acid (dodecanoic acid), C$_{13}$ tridecanoic acid, isotridecanoic acid, C$_{14}$ myristic acid (tetradecanoic acid), C$_{16}$ palmitic acid (hexadecanoic acid), C$_{17}$ margaric acid (heptadecanoic acid), C$_{18}$ stearic acid (octadecanoic acid), iso-stearic acid, C$_{20}$ arachidic acid (eicosanoic acid), C$_{21}$ heneicosanoic acid, C$_{22}$ behenic acid (docosanoic acid), C$_{24}$ lignoceric acid (tetracosanoic acid). As discussed above, such fatty acids may be present in the form of fatty acid esters (such as glyceride), free fatty acids, or combinations thereof.

Examples of unsaturated fatty acids include but are not limited to myristoleic acid (14:1), palmitoleic acid (16:1), oleic acid (18:1), petroselinic acid (18:1), ricinoleic acid (18:1), linoleic acid (18:2), linolenic acid (18:3), eleosteric acid (18:3), eoleic acid (18:1), gadoleic acid (20:1), arachidonic acid (20:4), eicosapentaenoic (20:5), and erucic acid (22:1). Unsaturated fatty acids are usually derived from plant or animal sources and comprise alkyl chains containing from 16 to 22 carbon atoms and 0-3 double bonds with the characteristic terminal carboxyl group. Typical plant and animal sources include, but are not limited to including lard, tallow, fat, borage oil, canola oil, castor oil, coconut oil, corn oil, cottonseed oil, hemp oil, linseed oil, macadamia oil, menhaden oil, olive oil, peanut oil, primrose oil, rapeseed oil, sardine oil, safflower oil, sesame seed oil, soybean oil, sunflower oil, palm oil, and palm kernel oil. As discussed above, such fatty acids may be present in the form of fatty acid esters (such as glyceride), free fatty acids, or combinations thereof. Further, dimerized and trimerized fatty acids are also contemplated. In general, they comprise the dimerization or trimerization products of ethylenically unsaturated fatty acids. Typical of the commercially available materials are materials known as "Empol 1010", "Empol 1014", "Empol 1022" and "Empol 1024" available from Emery Industries, Inc.

Amidoamines

In one aspect of the present invention, the fatty acid ester, fatty acid, or combinations thereof are reacted in the presence of the catalyst described herein with a diamine having at least one active hydrogen to form a fatty amidoamine. A preferred amidoamine is provided according to:

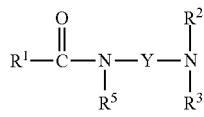

wherein $R^1$ is a saturated or unsaturated, straight or branched chain alkyl having from about 5 to about 25 carbon atoms (preferably about 9 to about 21 carbon atoms, and more preferably still from about 11 to about 17 carbon atoms) and optionally substituted with one or more hydroxyls;

wherein $R^2$ and $R^3$ are independently selected from the group consisting of hydrogen or lower alkyl optionally substituted with one or more hydroxyls or alkoxylated hydroxyls (preferably methyl, ethyl, —$CH_2CH_2OH$, or —$CH_2CH_2(OCH_2CH_2)_nOH$ wherein n is an integer from 1 to 5), and at least one of $R^2$ and $R^3$ is not hydrogen;

wherein $R^5$ is hydrogen or alkyl (preferably hydrogen or lower alkyl); and wherein Y is alkyl (preferably lower alkyl).

Still more preferably, the amidoamine is defined according to:

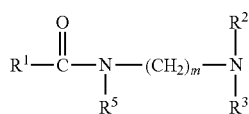

wherein $R^1$ is a saturated or unsaturated, straight or branched chain alkyl having from about 5 to about 25 carbon atoms (preferably about 9 to about 21 carbon atoms, and more preferably still from about 11 to about 17 carbon atoms) and optionally substituted with one or more hydroxyls;

wherein $R^2$ and $R^3$ are independently selected from the group consisting of hydrogen or lower alkyl optionally substituted with one or more hydroxyls or alkoxylated hydroxyls (preferably methyl, ethyl, —$CH_2CH_2OH$, or —$CH_2CH_2(OCH_2CH_2)_nOH$ wherein n is an integer from 1 to 5), and at least one of $R^2$ and $R^3$ is not hydrogen;

wherein $R^5$ is hydrogen or alkyl (preferably hydrogen or lower alkyl); and wherein m is 1, 2, 3, 4, 5, or 6 (preferably 2 or 3).

The amidoamine product composition formed using the catalyst described herein has superior physical properties compared to those using alkaline catalysts, such as sodium methylate. For example, the reaction of DMAPA and triglyceride yields a cocoamidopropyldimethylamine/glycerol product composition which typically has a viscosity less than 1000 cPs, preferably less than 500 cPs, and even more preferably less than 300 cPs, and typically a viscosity of about 150 to 250 cPs when measured at 12 RPM using a spindle #3 using a Brookfield rheometer. The freezing point is also less than about 50° F., and preferably less than 40° F.

Amides

In another aspect of the present invention, the fatty acid ester, fatty acid, or combinations thereof are reacted in the presence of the catalyst described herein with a monoamine having at least one active hydrogen to form a fatty amide. A preferred amide is provided according to:

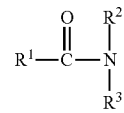

wherein $R^1$ is a saturated or unsaturated, straight or branched chain alkyl having from about 5 to about 25 carbon atoms (preferably about 9 to about 21 carbon atoms, and more preferably still from about 11 to about 17 carbon atoms) and optionally substituted with one or more hydroxyls; and wherein $R^2$ and $R^3$ are independently selected from the group consisting of hydrogen or lower alkyl optionally substituted with one or more hydroxyls or alkoxylated hydroxyls (preferably methyl, ethyl, —$CH_2CH_2OH$, or —$CH_2CH_2(OCH_2CH_2)_nOH$ wherein n is an integer from 1 to 5), and at least one of $R^2$ and $R^3$ is not hydrogen.

The amidoamines and the amides formed using the catalyst in accordance with the present invention may be used to form a large number of derivatives having superior physical properties in the product composition. For example, in one aspect, the amidoamines can readily be cyclized in the presence of heat to form the corresponding imidazolines. For example, in one aspect, imidazolines according to the following formula are provided.

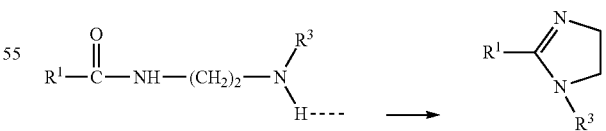

wherein $R^1$ is a saturated or unsaturated, straight or branched chain alkyl having from about 5 to about 25 carbon atoms (preferably about 9 to about 21 carbon atoms, and more preferably still from about 11 to about 17 carbon atoms) and optionally substituted with one or more hydroxyls; and wherein $R^3$ is selected from the group consisting of hydrogen or lower alkyl optionally substituted with one or more hydroxyls or alkoxylated hydroxyls (preferably methyl, ethyl, —CH$_2$CH$_2$OH, or —CH$_2$CH$_2$(OCH$_2$CH$_2$)$_n$OH wherein n is an integer from 1 to 5).

The most preferred imidazolines are those wherein R$^3$ is —CH$_2$CH$_2$OH.

As another example, the amidoamines can readily be oxidized to form corresponding amidoamine oxides, for example by the addition of hydrogen peroxide. In one aspect, the amidoamine oxides according to the following formula are provided:

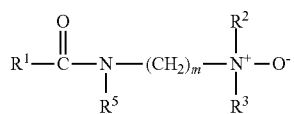

wherein R$^1$ is a saturated or unsaturated, straight or branched chain alkyl having from about 5 to about 25 carbon atoms (preferably about 9 to about 21 carbon atoms, and more preferably still from about 11 to about 17 carbon atoms) and optionally substituted with one or more hydroxyls;

wherein R$^2$ and R$^3$ are independently selected from the group consisting of hydrogen or lower alkyl optionally substituted with one or more hydroxyls or alkoxylated hydroxyls (preferably methyl, ethyl, —CH$_2$CH$_2$OH, or —CH$_2$CH$_2$(OCH$_2$CH$_2$)$_n$OH wherein n is an integer from 1 to 5), and at least one of R$^2$ and R$^3$ is not hydrogen;

wherein R$^5$ is hydrogen or alkyl (preferably hydrogen or lower alkyl); and wherein m is 1, 2, 3, 4, 5, or 6 (preferably 2 or 3).

As yet another example, the amidoamines (and corresponding imidazolines) can be quaternized. Quaternization is carried out under conditions and with reactants generally familiar to those experienced in this field. For example, the quaternizing agent may have the formula R$^7$X, wherein R$^7$ is an alkyl or aralkyl optionally containing a hydroxy or alkoxy (preferably R$^7$ is methyl, benzyl, ethyl, or hydroxyalkyl), and X is a suitable leaving group, such as a halide or alkyl sulfate (preferably chloride, bromide, methyl sulfate, or nitrate). Preferably, R$^7$X is methyl chloride, benzyl chloride, dimethyl sulfate, diethyl sulfate, or chloroethanol. Thus, in one aspect, compounds according to the following are provided:

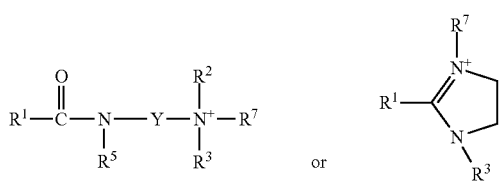

wherein R$^1$ is a saturated or unsaturated, straight or branched chain alkyl having from about 5 to about 25 carbon atoms (preferably about 9 to about 21 carbon atoms, and more preferably still from about 11 to about 17 carbon atoms) and optionally substituted with one or more hydroxyls;

wherein R$^2$ and R$^3$ are independently selected from the group consisting of hydrogen or lower alkyl optionally substituted with one or more hydroxyls or alkoxylated hydroxyls (preferably methyl, ethyl, —CH$_2$CH$_2$OH, or —CH$_2$CH$_2$(OCH$_2$CH$_2$)$_n$OH wherein n is an integer from 1 to 5), and at least one of R$^2$ and R$^3$ is not hydrogen;

wherein R$^5$ is hydrogen or alkyl (preferably hydrogen or lower alkyl); and wherein m is 1, 2, 3, 4, 5, or 6 (preferably 2 or 3);

wherein R$^7$ is alkyl or aralkyl optionally containing a hydroxy or alkoxy; and wherein Y is alkyl (preferably lower alkyl).

Use of Catalysts to Prepare Surfactants

The amidoamines formed using the catalyst of the present invention may also be readily converted into amphoteric surfactants, such as betaines, sulfobetaines (sultaines), sulfitobetaines, sulfatobetaines, phosphinate betaines, phosphonate betaines, phosphitobetaines, phosphatobetaines, and the like. Such compounds can be readily prepared by reacting the appropriate haloalkylanionic salt (for example sodium monochloroacetate, sodium 3-chloro-2-hydroxypropanesulfonate, sodium 3-chloro-2-hydroxy-propanephosphinate) as described herein.

Exemplary amphoteric surfactants having the following structure can thus be prepared:

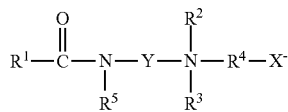

wherein R$^1$ is a saturated or unsaturated, straight or branched chain alkyl having from about 5 to about 25 carbon atoms (preferably about 9 to about 21 carbon atoms, and more preferably still from about 11 to about 17 carbon atoms) and optionally substituted with one or more hydroxyls;

wherein R$^2$ and R$^3$ are independently selected from the group consisting of hydrogen or lower alkyl optionally substituted with one or more hydroxyls or alkoxylated hydroxyls (preferably methyl, ethyl, —CH$_2$CH$_2$OH, or —CH$_2$CH$_2$(OCH$_2$CH$_2$)$_n$OH wherein n is an integer from 1 to 5), and at least one of R$^2$ and R$^3$ is not hydrogen;

wherein X$^-$ is selected from the group consisting of —CO$_2^-$ (betaine), —SO$_2$O$^-$ (sulfobetaine or sultaine), —OSO$_2^-$ (sulfitobetaine), —OSO$_3^-$ (sulfatobetaine), —PR$^6$O$_2^-$ (phosphinatebetaine), —P(OR$^6$)O$_2^-$ (phosphonatebetaine), —OP(O)(R$^6$)O$^-$ (phosphitobetaine), and —OP(O)(OR$^6$)O$^-$ (phosphatobetaine), and wherein R$^6$ is hydrogen or lower alkyl.

wherein R$^4$ is selected from the group consisting of saturated or unsaturated, straight or branched chain lower alkyl, optionally substituted with one or more hydroxys (when X$^-$ is CO$_2^-$, R$^4$ preferably has 1 or 3 carbon atoms, more preferably 1 carbon atom);

wherein R$^5$ is hydrogen or lower alkyl; and wherein Y is alkyl (preferably lower alkyl).

Still more preferably, the amphoteric compounds are defined according to:

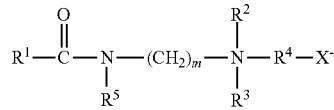

wherein R$^1$ is a saturated or unsaturated, straight or branched chain alkyl having from about 5 to about 25 carbon atoms (preferably about 9 to about 21 carbon atoms, and more preferably still from about 11 to about 17 carbon atoms) and optionally substituted with one or more hydroxyls;

wherein R$^2$ and R$^3$ are independently selected from the group consisting of hydrogen or lower alkyl optionally substituted with one or more hydroxyls or alkoxylated hydroxyls (preferably methyl, ethyl, —CH$_2$CH$_2$OH, or —CH$_2$CH$_2$ (OCH₂CH₂)$_n$OH wherein n is an integer from 1 to 5), and at least one of $R^2$ and $R^3$ is not hydrogen;

wherein $X^-$ is selected from the group consisting of —$CO_2^-$ (betaine), —$SO_2O^-$ (sulfobetaine or sultaine), —$OSO_2^-$ (sulfitobetaine), —$OSO_3^-$ (sulfatobetaine), —$PR^6O_2^-$ (phosphinatebetaine), —$P(OR^6)O_2^-$ (phosphonatebetaine), —$OP(O)(R^6)O^-$ (phosphitobetaine), and —$OP(O)(OR^6)O^-$ (phosphatobetaine), and wherein $R^6$ is hydrogen or lower alkyl;

wherein $R^4$ is selected from the group consisting of saturated or unsaturated, straight or branched chain lower alkyl, optionally substituted with hydroxyl (When $X^-$ is $CO_2^-$, $R^4$ preferably has 1 or 3 carbon atoms, more preferably 1 carbon atom);

wherein $R^5$ is hydrogen or lower alkyl; and wherein m is 1, 2, 3, 4, 5, or 6 (preferably 2 or 3).

Betaines

One example of the amphoteric surfactants that can be prepared using the process of the present invention includes the betaines according to:

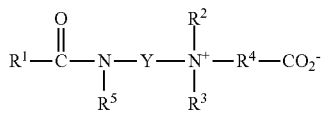

wherein $R^1$ is a saturated or unsaturated, straight or branched chain alkyl having from about 5 to about 25 carbon atoms (preferably about 9 to about 21 carbon atoms, and more preferably still from about 11 to about 17 carbon atoms) and optionally substituted with one or more hydroxyls;

wherein $R^2$ and $R^3$ are independently selected from the group consisting of hydrogen or lower alkyl optionally substituted with one or more hydroxyls or alkoxylated hydroxyls (preferably methyl, ethyl, —$CH_2CH_2OH$, or —$CH_2CH_2$(OCH₂CH₂)$_n$OH wherein n is an integer from 1 to 5), and at least one of $R^2$ and $R^3$ is not hydrogen;

wherein $R^4$ is selected from the group consisting of saturated or unsaturated, straight or branched chain lower alkyl, optionally substituted with hydroxyl;

wherein $R^5$ is hydrogen or lower alkyl; and wherein Y is alkyl (preferably lower alkyl).

More preferably, the betaine is one defined according to:

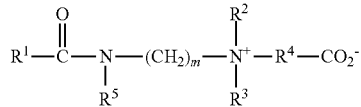

wherein $R^1$ is a saturated or unsaturated, straight or branched chain alkyl having from about 5 to about 25 carbon atoms (preferably about 9 to about 21 carbon atoms, and more preferably still from about 11 to about 17 carbon atoms) and optionally substituted with one or more hydroxyls;

wherein $R^2$ and $R^3$ are independently selected from the group consisting of hydrogen or lower alkyl optionally substituted with one or more hydroxyls or alkoxylated hydroxyls (preferably methyl, ethyl, —$CH_2CH_2OH$, or —$CH_2CH_2$(OCH₂CH₂)$_n$OH wherein n is an integer from 1 to 5), and at least one of $R^2$ and $R^3$ is not hydrogen;

wherein $R^4$ is selected from the group consisting of saturated or unsaturated, straight or branched chain lower alkyl, optionally substituted with hydroxyl;

wherein $R^5$ is hydrogen or lower alkyl; and wherein m is 1, 2, 3, 4, 5, or 6 (preferably 2 or 3).

Most preferably, the betaine is an alkylamidopropylbetaine according to:

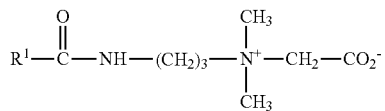

wherein $R^1$ is a saturated or unsaturated, straight or branched chain alkyl having from about 5 to about 25 carbon atoms (preferably about 9 to about 21 carbon atoms, and more preferably still from about 11 to about 17 carbon atoms) and optionally substituted with one or more hydroxyls.

A most preferred alkylamidopropylbetaine is cocoamidopropylbetaine.

The amidoamine intermediates formed using the catalyst as described herein can be advantageously treated with various haloalkylcarboxylate salt, such as sodium chloroacetate, producing the corresponding betaines. The beneficial physical attributes which leads to processing advantages for the amidoamines are translated into the corresponding betaines.

Sultaines

Another example of amphoteric surfactants that can be formed using the process of the present invention are the sulfobetaines (sultaines), such as one according to:

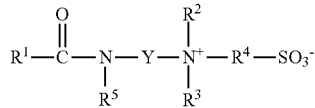

wherein $R^1$ is a saturated or unsaturated, straight or branched chain alkyl having from about 5 to about 25 carbon atoms (preferably about 9 to about 21 carbon atoms, and more preferably still from about 11 to about 17 carbon atoms) and optionally substituted with one or more hydroxyls;

wherein $R^2$ and $R^3$ are independently selected from the group consisting of hydrogen or lower alkyl optionally substituted with one or more hydroxyls or alkoxylated hydroxyls (preferably methyl, ethyl, —$CH_2CH_2OH$, or —$CH_2CH_2$(OCH₂CH₂)$_n$OH wherein n is an integer from 1 to 5), and at least one of $R^2$ and $R^3$ is not hydrogen;

wherein $R^4$ is selected from the group consisting of saturated or unsaturated, straight or branched chain lower alkyl, optionally substituted with hydroxyl;

wherein $R^5$ is hydrogen or lower alkyl; and wherein Y is alkyl (preferably lower alkyl).

In another aspect, the sultaines are alkylamidoalkylsultaines according to:

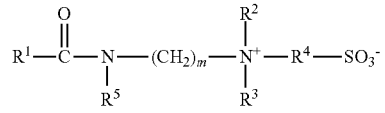

wherein $R^1$ is a saturated or unsaturated, straight or branched chain alkyl having from about 5 to about 25 carbon atoms (preferably about 9 to about 21 carbon atoms, and more preferably still from about 11 to about 17 carbon atoms) and optionally substituted with one or more hydroxyls;

wherein $R^2$ and $R^3$ are independently selected from the group consisting of hydrogen or lower alkyl optionally substituted with one or more hydroxyls or alkoxylated hydroxyls (preferably methyl, ethyl, —CH$_2$CH$_2$OH, or —CH$_2$CH$_2$(OCH$_2$CH$_2$)$_n$OH wherein n is an integer from 1 to 5), and at least one of R$^2$ and R$^3$ is not hydrogen;

wherein R$^4$ is selected from the group consisting of saturated or unsaturated, straight or branched chain lower alkyl, optionally substituted with hydroxyl;

wherein R$^5$ is hydrogen or lower alkyl; and wherein m is 1, 2, 3, 4, 5, or 6 (preferably 2 or 3).

Most preferably, the sultaine is a hydroxylsultaine, such as one according to:

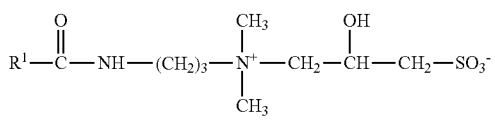

wherein R$^1$ is a saturated or unsaturated, straight or branched chain alkyl having from about 5 to about 25 carbon atoms (preferably about 9 to about 21 carbon atoms, and more preferably still from about 11 to about 17 carbon atoms) and optionally substituted with one or more hydroxyls.

The amidoamine intermediates formed using the catalyst as described herein can be advantageously treated with various haloalkylsulfonate salts or sultones (cyclic sulfonates, such as gamma sultone) producing the corresponding sultaines. The beneficial physical attributes which leads to processing advantages for the amidoamines are translated into the corresponding sultaines.

Sulfitobetaines

Another example of amphoteric surfactants that can be formed using the process of the present invention are the sulfitobetaines, such as one according to:

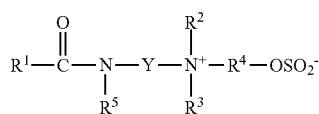

wherein R$^1$ is a saturated or unsaturated, straight or branched chain alkyl having from about 5 to about 25 carbon atoms (preferably about 9 to about 21 carbon atoms, and more preferably still from about 11 to about 17 carbon atoms) and optionally substituted with one or more hydroxyls;

wherein R$^2$ and R$^3$ are independently selected from the group consisting of hydrogen or lower alkyl optionally substituted with one or more hydroxyls or alkoxylated hydroxyls (preferably methyl, ethyl, —CH$_2$CH$_2$OH, or —CH$_2$CH$_2$(OCH$_2$CH$_2$)$_n$OH wherein n is an integer from 1 to 5), and at least one of R$^2$ and R$^3$ is not hydrogen;

wherein R$^4$ is selected from the group consisting of saturated or unsaturated, straight or branched chain lower alkyl, optionally substituted with hydroxyl;

wherein R$^5$ is hydrogen or lower alkyl; and wherein Y is alkyl (preferably lower alkyl).

In another aspect, the sulfitobetaines are alkylamidoalkyl-sufitobetaines according to:

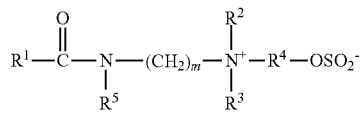

wherein R$^1$ is a saturated or unsaturated, straight or branched chain alkyl having from about 5 to about 25 carbon atoms (preferably about 9 to about 21 carbon atoms, and more preferably still from about 11 to about 17 carbon atoms) and optionally substituted with one or more hydroxyls;

wherein R$^2$ and R$^3$ are independently selected from the group consisting of hydrogen or lower alkyl optionally substituted with one or more hydroxyls or alkoxylated hydroxyls (preferably methyl, ethyl, —CH$_2$CH$_2$OH, or —CH$_2$CH$_2$(OCH$_2$CH$_2$)$_n$OH wherein n is an integer from 1 to 5), and at least one of R$^2$ and R$^3$ is not hydrogen;

wherein R$^4$ is selected from the group consisting of saturated or unsaturated, straight or branched chain lower alkyl, optionally substituted with hydroxyl;

wherein R$^5$ is hydrogen or lower alkyl; and wherein m is 1, 2, 3, 4, 5, or 6 (preferably 2 or 3).

Most preferably, the sulfitobetaine is a hydroxylsulfitobetaine, such as one according to:

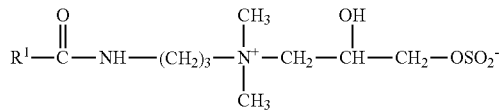

wherein R$^1$ is a saturated or unsaturated, straight or branched chain alkyl having from about 5 to about 25 carbon atoms and optionally substituted with one or more hydroxyls.

The amidoamine intermediates formed using the catalyst as described herein can be advantageously treated with various haloalkylsulfite salts producing the corresponding sulfitobetaines. The beneficial physical attributes which leads to processing advantages for the amidoamines are translated into the corresponding sulfitobetaines.

Sulfatobetaines

Another example of amphoteric surfactants that can be formed using the process of the present invention are the sulfatobetaines, such as one according to:

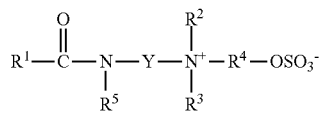

wherein R$^1$ is a saturated or unsaturated, straight or branched chain alkyl having from about 5 to about 25 carbon atoms (preferably about 9 to about 21 carbon atoms, and more preferably still from about 11 to about 17 carbon atoms) and optionally substituted with one or more hydroxyls;

wherein R$^2$ and R$^3$ are independently selected from the group consisting of hydrogen or lower alkyl optionally substituted with one or more hydroxyls or alkoxylated hydroxyls (preferably methyl, ethyl, —CH$_2$CH$_2$OH, or —CH$_2$CH$_2$(OCH$_2$CH$_2$)$_n$OH wherein n is an integer from 1 to 5), and at least one of R$^2$ and R$^3$ is not hydrogen;

wherein R$^4$ is selected from the group consisting of saturated or unsaturated, straight or branched chain lower alkyl, optionally substituted with hydroxyl;

wherein $R^5$ is hydrogen or lower alkyl; and wherein Y is alkyl (preferably lower alkyl).

In another aspect, the sulfatobetaines are alkylamidoalkylsulfatobetaines according to:

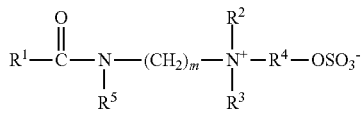

wherein $R^1$ is a saturated or unsaturated, straight or branched chain alkyl having from about 5 to about 25 carbon atoms (preferably about 9 to about 21 carbon atoms, and more preferably still from about 11 to about 17 carbon atoms) and optionally substituted with one or more hydroxyls;

wherein $R^2$ and $R^3$ are independently selected from the group consisting of hydrogen or lower alkyl optionally substituted with one or more hydroxyls or alkoxylated hydroxyls (preferably methyl, ethyl, —$CH_2CH_2OH$, or —$CH_2CH_2(OCH_2CH_2)_nOH$ wherein n is an integer from 1 to 5), and at least one of $R^2$ and $R^3$ is not hydrogen;

wherein $R^4$ is selected from the group consisting of saturated or unsaturated, straight or branched chain lower alkyl, optionally substituted with hydroxyl;

wherein $R^5$ is hydrogen or lower alkyl; and wherein m is 1, 2, 3, 4, 5, or 6 (preferably 2 or 3).

Most preferably, the sulfatobetaine is a hydroxylsulfatobetaine, such as one according to:

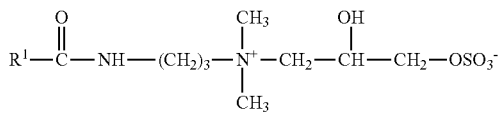

wherein $R^1$ is a saturated or unsaturated, straight or branched chain alkyl having from about 5 to about 25 carbon atoms and optionally substituted with one or more hydroxyls.

The amidoamine intermediates formed using the catalyst as described herein can be advantageously treated with various haloalkylsulfate salts or cyclic sulfates, producing the corresponding sulfatobetaines. The beneficial physical attributes which leads to processing advantages for the amidoamines are translated into the corresponding sulfatobetaines.

Phosphinate Betaines

Another example of amphoteric surfactants that can be formed using the process of the present invention are the phosphinate betaines, such as one according to:

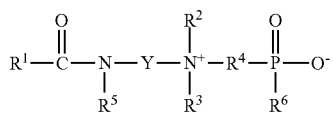

wherein $R^1$ is a saturated or unsaturated, straight or branched chain alkyl having from about 5 to about 25 carbon atoms (preferably about 9 to about 21 carbon atoms, and more preferably still from about 11 to about 17 carbon atoms) and optionally substituted with one or more hydroxyls;

wherein $R^2$ and $R^3$ are independently selected from the group consisting of hydrogen or lower alkyl optionally substituted with one or more hydroxyls or alkoxylated hydroxyls (preferably methyl, ethyl, —$CH_2CH_2OH$, or —$CH_2CH_2(OCH_2CH_2)_nOH$ wherein n is an integer from 1 to 5), and at least one of $R^2$ and $R^3$ is not hydrogen;

wherein $R^4$ is selected from the group consisting of saturated or unsaturated, straight or branched chain lower alkyl, optionally substituted with hydroxyl;

wherein $R^5$ is hydrogen or lower alkyl;

wherein $R^6$ is hydrogen or lower alkyl; and wherein Y is alkyl (preferably lower alkyl).

In another aspect, the phosphinate betaines are those defined according to:

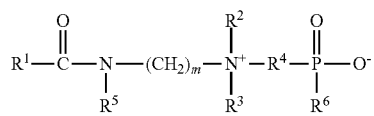

wherein $R^1$ is a saturated or unsaturated, straight or branched chain alkyl having from about 5 to about 25 carbon atoms (preferably about 9 to about 21 carbon atoms, and more preferably still from about 11 to about 17 carbon atoms) and optionally substituted with one or more hydroxyls;

wherein $R^2$ and $R^3$ are independently selected from the group consisting of hydrogen or lower alkyl optionally substituted with one or more hydroxyls or alkoxylated hydroxyls (preferably methyl, ethyl, —$CH_2CH_2OH$, or —$CH_2CH_2(OCH_2CH_2)_nOH$ wherein n is an integer from 1 to 5), and at least one of $R^2$ and $R^3$ is not hydrogen;

wherein $R^4$ is selected from the group consisting of saturated or unsaturated, straight or branched chain lower alkyl, optionally substituted with hydroxyl;

wherein $R^5$ is hydrogen or lower alkyl;

wherein $R^6$ is hydrogen or lower alkyl; and wherein m is 1, 2, 3, 4, 5, or 6 (preferably 2 or 3).

Most preferably, the phosphinate betaine is a hydroxylphosphinate betaine, such as one according to:

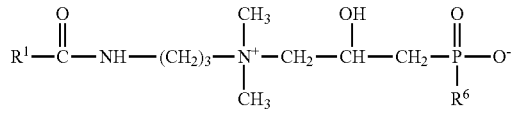

wherein $R^1$ is a saturated or unsaturated, straight or branched chain alkyl having from about 5 to about 25 carbon atoms and optionally substituted with one or more hydroxyls.

The amidoamine intermediates formed using the catalyst as described herein can be advantageously treated with various haloalkylphosphinate salts producing the corresponding phosphinate betaines. The beneficial physical attributes which leads to processing advantages for the amidoamines are translated into the corresponding phosphinate betaines.

Phosphonate Betaines

Another example of amphoteric surfactants that can be formed using the process of the present invention are the phosphonate betaines, such as one according to:

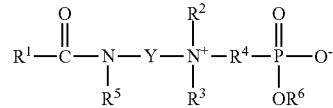

wherein $R^1$ is a saturated or unsaturated, straight or branched chain alkyl having from about 5 to about 25 carbon atoms (preferably about 9 to about 21 carbon atoms, and more preferably still from about 11 to about 17 carbon atoms) and optionally substituted with one or more hydroxyls;

wherein $R^2$ and $R^3$ are independently selected from the group consisting of hydrogen or lower alkyl optionally substituted with one or more hydroxyls or alkoxylated hydroxyls (preferably methyl, ethyl, —CH$_2$CH$_2$OH, or —CH$_2$CH$_2$(OCH$_2$CH$_2$)$_n$OH wherein n is an integer from 1 to 5), and at least one of $R^2$ and $R^3$ is not hydrogen;

wherein $R^4$ is selected from the group consisting of saturated or unsaturated, straight or branched chain lower alkyl, optionally substituted with hydroxyl;

wherein $R^5$ is hydrogen or lower alkyl;

wherein $R^6$ is hydrogen or lower alkyl; and wherein Y is alkyl (preferably lower alkyl).

In another aspect, the phosphonate betaines are those defined according to:

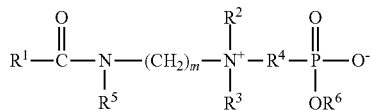

wherein $R^1$ is a saturated or unsaturated, straight or branched chain alkyl having from about 5 to about 25 carbon atoms (preferably about 9 to about 21 carbon atoms, and more preferably still from about 11 to about 17 carbon atoms) and optionally substituted with one or more hydroxyls;

wherein $R^2$ and $R^3$ are independently selected from the group consisting of hydrogen or lower alkyl optionally substituted with one or more hydroxyls or alkoxylated hydroxyls (preferably methyl, ethyl, —CH$_2$CH$_2$OH, or —CH$_2$CH$_2$(OCH$_2$CH$_2$)$_n$OH wherein n is an integer from 1 to 5), and at least one of $R^2$ and $R^3$ is not hydrogen;

wherein $R^4$ is selected from the group consisting of saturated or unsaturated, straight or branched chain lower alkyl, optionally substituted with hydroxyl;

wherein $R^5$ is hydrogen or lower alkyl;

wherein $R^6$ is hydrogen or lower alkyl; and wherein m is 1, 2, 3, 4, 5, or 6 (preferably 2 or 3).

Most preferably, the phosphonate betaine is a hydroxyl-phosphonate betaine, such as one according to:

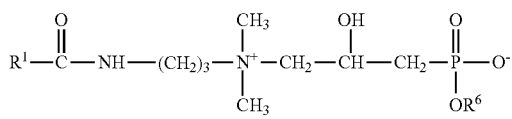

wherein $R^1$ is a saturated or unsaturated, straight or branched chain alkyl having from about 5 to about 25 carbon atoms and optionally substituted with one or more hydroxyls.

The amidoamine intermediates formed using the catalyst as described herein can be advantageously treated with various haloalkylphosphonate salts producing the corresponding phosphonate betaines. The beneficial physical attributes which leads to processing advantages for the amidoamines are translated into the corresponding phosphonate betaines.

Phosphitobetaines

Another example of amphoteric surfactants that can be formed using the process of the present invention are the phosphitobetaines, such as one according to:

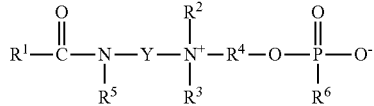

wherein $R^1$ is a saturated or unsaturated, straight or branched chain alkyl having from about 5 to about 25 carbon atoms (preferably about 9 to about 21 carbon atoms, and more preferably still from about 11 to about 17 carbon atoms) and optionally substituted with one or more hydroxyls;

wherein $R^2$ and $R^3$ are independently selected from the group consisting of hydrogen or lower alkyl optionally substituted with one or more hydroxyls or alkoxylated hydroxyls (preferably methyl, ethyl, —CH$_2$CH$_2$OH, or —CH$_2$CH$_2$(OCH$_2$CH$_2$)$_n$OH wherein n is an integer from 1 to 5), and at least one of $R^2$ and $R^3$ is not hydrogen;

wherein $R^4$ is selected from the group consisting of saturated or unsaturated, straight or branched chain lower alkyl, optionally substituted with hydroxyl;

wherein $R^5$ is hydrogen or lower alkyl;

wherein $R^6$ is hydrogen; and wherein Y is alkyl (preferably lower alkyl).

In another aspect, the phosphitobetaines are those defined according to:

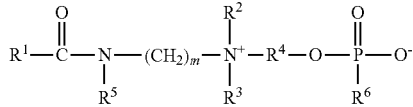

wherein $R^1$ is a saturated or unsaturated, straight or branched chain alkyl having from about 5 to about 25 carbon atoms (preferably about 9 to about 21 carbon atoms, and more preferably still from about 11 to about 17 carbon atoms) and optionally substituted with one or more hydroxyls;

wherein $R^2$ and $R^3$ are independently selected from the group consisting of hydrogen or lower alkyl optionally substituted with one or more hydroxyls or alkoxylated hydroxyls (preferably methyl, ethyl, —CH$_2$CH$_2$OH, or —CH$_2$CH$_2$(OCH$_2$CH$_2$)$_n$OH wherein n is an integer from 1 to 5), and at least one of $R^2$ and $R^3$ is not hydrogen;

wherein $R^4$ is selected from the group consisting of saturated or unsaturated, straight or branched chain lower alkyl, optionally substituted with hydroxyl;

wherein $R^5$ is hydrogen or lower alkyl;

wherein $R^6$ is hydrogen; and wherein m is 1, 2, 3, 4, 5, or 6 (preferably 2 or 3).

Most preferably, the phosphitobetaine is a hydroxyl-phosphitobetaine, such as one according to:

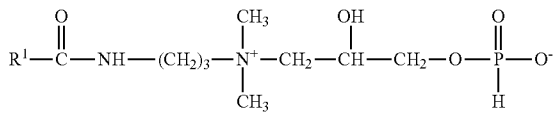

wherein $R^1$ is a saturated or unsaturated, straight or branched chain alkyl having from about 5 to about 25 carbon atoms and optionally substituted with one or more hydroxyls.

The amidoamine intermediates formed using the catalyst as described herein can be advantageously treated with various haloalkylphosphite salts producing the corresponding phosphitobetaines. The beneficial physical attributes which leads to processing advantages for the amidoamines are translated into the corresponding phosphitobetaines.

Phosphatobetaines

Another example of amphoteric surfactants that can be formed using the process of the present invention are the phosphatobetaines, such as one according to:

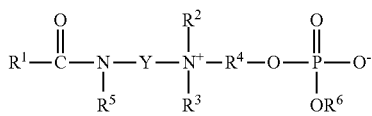

wherein $R^1$ is a saturated or unsaturated, straight or branched chain alkyl having from about 5 to about 25 carbon atoms (preferably about 9 to about 21 carbon atoms, and more preferably still from about 11 to about 17 carbon atoms) and optionally substituted with one or more hydroxyls;

wherein $R^2$ and $R^3$ are independently selected from the group consisting of hydrogen or lower alkyl optionally substituted with one or more hydroxyls or alkoxylated hydroxyls (preferably methyl, ethyl, —$CH_2CH_2OH$, or —$CH_2CH_2(OCH_2CH_2)_nOH$ wherein n is an integer from 1 to 5), and at least one of $R^2$ and $R^3$ is not hydrogen;

wherein $R^4$ is selected from the group consisting of saturated or unsaturated, straight or branched chain lower alkyl, optionally substituted with hydroxyl;

wherein $R^5$ is hydrogen or lower alkyl;

wherein $R^6$ is hydrogen; and wherein Y is alkyl (preferably lower alkyl).

In another aspect, the phosphatobetaines are those defined according to:

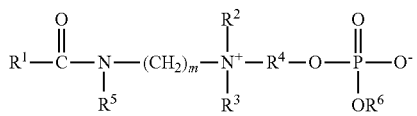

wherein $R^1$ is a saturated or unsaturated, straight, or branched chain alkyl having from about 5 to about 25 carbon atoms (preferably about 9 to about 21 carbon atoms, and more preferably still from about 11 to about 17 carbon atoms) and optionally substituted with one or more hydroxyls;

wherein $R^2$ and $R^3$ are independently selected from the group consisting of hydrogen or lower alkyl optionally substituted with one or more hydroxyls or alkoxylated hydroxyls (preferably methyl, ethyl, —$CH_2CH_2OH$, or —$CH_2CH_2(OCH_2CH_2)_nOH$ wherein n is an integer from 1 to 5), and at least one of $R^2$ and $R^3$ is not hydrogen;

wherein $R^4$ is selected from the group consisting of saturated or unsaturated, straight or branched chain lower alkyl, optionally substituted with hydroxyl;

wherein $R^5$ is hydrogen or lower alkyl;

wherein $R^6$ is hydrogen; and wherein m is 1, 2, 3, 4, 5, or 6 (preferably 2 or 3).

Most preferably, the phosphatobetaine is a hydroxyl-phosphatobetaine, such as one according to:

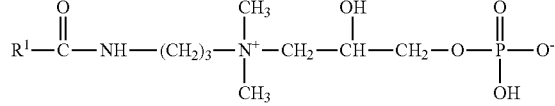

wherein $R^1$ is a saturated or unsaturated, straight or branched chain alkyl having from about 5 to about 25 carbon atoms and optionally substituted with one or more hydroxyls.

The amidoamine intermediates formed using the catalyst as described herein can be advantageously treated with various haloalkylphosphate salts producing the corresponding phosphatobetaines. The beneficial physical attributes which leads to processing advantages for the amidoamines are translated into the corresponding phosphatobetaines.

To further illustrate the invention, the following non-limiting examples are provided.

Example 1

Preparation of Catalyst

This example is described in Weerasooriya et al., U.S. Pat. No. 7,119,236, which is incorporated by reference in its entirety. In this example, a catalyst in accordance with the present invention and having the composition set forth in Table 1 was prepared in a batch process. The catalyst is referred to herein as the "U-Cat."

To prepare the catalyst, a three-neck round bottom flask is equipped with a magnetic stir bar, a glass stopper, a Dean-Stark trap filled with n-butanol, a condenser topped with a calcium chloride drying tube, and is placed in an oil bath. The n-butanol is charged to the flask and stirring is initiated. The calcium hydroxide is slowly added, and allowed to stir for 15 minutes. A carboxylic acid (such as 2-ethylhexanoic acid) is then added to the mixture via syringe. The flask containing the mixture is then heated to above 120° C. at atmospheric pressure. The stirring suspension is allowed to reflux for up to about 8 hours. Under these conditions, water and the dispersing medium will be removed during the process, but the dispersing medium is recycled into the reaction vessel. After cooling to room temperature, the stir bar is removed, and an overhead stirrer is added. The Dean-Stark trap, condenser, drying tube, oil bath, and stoppers are removed. A source of nitrogen, thermometer, water bath, and presser equalizing dropping funnel are added. The pressure equalizing dropping funnel is charged with an inorganic acid (such as sulfuric acid), and the acid is added over the course of about 3 hours. The internal temperature is maintained at or below about 25° C. by use of the water bath and ice. After the acid is added completely, the suspension is allowed to stir for an additional 30-60 minutes at a temperature of about 25° C. Optionally, the heating and/or the water removal steps can be omitted partially or completely.

TABLE 1

| Composition of Catalyst Formulation | |
|---|---|
| Component | % by mass |
| n-butanol | 72.8 |
| calcium hydroxide | 15.1 |
| 2-ethylhexanoic acid | 3.5 |
| sulfuric acid | 7.7 |

Example 2

Preparation Fatty Amides Using Catalyst

The standard manufacturing procedure for producing a key fatty amide involves the reaction of N,N-dimethylaminopropylamine ("DMAPA") with a triglyceride such as coconut oil under alkaline catalyst such as sodium methylate ($NaOCH_3$) at elevated temperatures. In this example, the milder U-Cat catalyst of Example 1 was substituted for the alkaline catalyst in order to ascertain the effect on the reaction products.

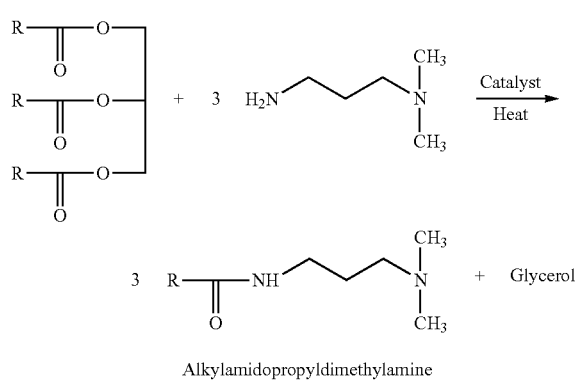

Alkylamidopropyldimethylamine

For the sodium methylate catalyzed process, a 2-gallon stainless steel autoclave equipped with an overhead stirrer, internal steam heating, water cooling, and a thermocouple was charged with coconut oil (1014 g). This was first heated to 210° F. with nitrogen purging with vacuum (about −5 psig) to dry the oil. Next, 20 g of NaOCH$_3$ (25% in methanol) was added and vacuum-nitrogen purged for 15 minutes at 211° F. in order to remove volatiles (methanol). The amine (DMAPA, 419 g) was added, pressurized to 1 psig with nitrogen and the temperature was raised from 211° F. to 285° F. The transamidation reaction progress was monitored by periodic sampling for amine value and was stopped when it reached 174. This reaction took approximately 4 hours.

For the U-Cat catalyzed process using the Catalyst of Example 1, the same procedure was employed except the catalyst level was lower and the temperature used was higher (240° F.) for removing volatiles (butanol) after the addition of the catalyst. The reaction took a little under 4 hours to reach an amine value of 174. The reaction mixture comprised coconut oil (1012 g), the U-Cat catalyst (10 g), and DMAPA (418 g).

As shown in Table 2, the product of the reaction using the U-Cat catalyst of Example 1 resulted in a less viscous, more clearly colored blend of the cocoamidopropyldimethylamine and glycerol. Thus, the product has superior physical properties.

TABLE 2

Alkylamidoalkylamine Products

| Catalyst | Viscosity, Spindle#3 12 rpm, 72° F. | Freeze Point | Appearance |
|---|---|---|---|
| U-Cat | 200 cPs | ~38° F. | Clear amber liquid |
| Sodium Methylate (comparative Ex.) | 2200 cPs | ~71° F. | Hazy Amber semi-solid |

The higher viscosity of the amidoamine for the prior art reaction can be explained by the formation of polyglycerol. The polyglycerol process shows facile reaction of glycerol under high alkalinity as generally described in U.S. Pat. No. 6,620,904. In order to achieve good reaction rates in the production of the amidoamine, following industry practice, however, a higher level of NaOCH$_3$ was employed compared to the U-Cat catalyst.

The U-Cat catalyst of Example 1 (and generally disclosed in U.S. Pat. No. 7,199,236) was found to be a mild, yet very effective catalyst. This is manifested in its ability to activate esters, for example methyl esters and triglycerides, for reaction with ethylene oxide. The mildness of U-Cat is exhibited by the fact that when U-Cat is used as an ethoxylation catalyst in the manufacture of alcohol ethoxylates, the resultant product comes out at neutral pH whereas NaOH and NaOCH$_3$ catalyzed versions result in products with pH values near 10, which necessitates acid neutralization.

Example 3

Preparation of Alkylamidoalkyl Betaines

In this example, the lower viscosity of the amidoamine of Example 2 is extended to the preparation of betaines having superior properties. In this regard, it is known that amphoteric surfactants, such as betaines, often behave as solid bodies as the concentration increases. For example, in EP 1672056, the importance of lowering of the viscosity is discussed in order to achieve self-preserving nature and savings on transportation and production cost. Most current processes can achieve only 35-36% solids levels before solidification. EP 1672056 utilizes additives such as acyl amino acids to reach 45% or more solids level. Further, U.S. Pat. No. 7,033,989 discusses the use of cyclodextrin as a viscosity reducer for betaines, amine oxides, and similar compounds.

In this example, betaine derivatives were formed using the products of Example 2. In general, this process is provided according to:

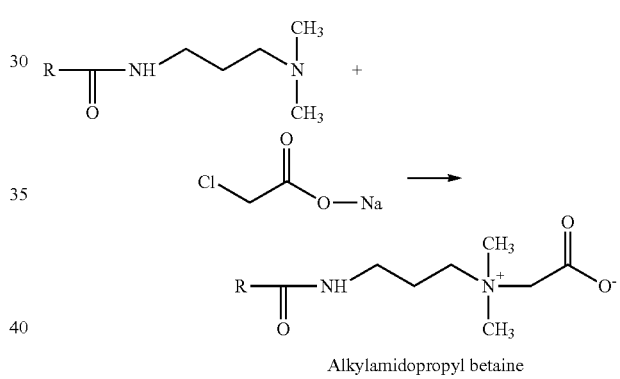

Alkylamidopropyl betaine

More specifically, for the betaine process in which the amidoamine composition was formed using the U-Cat catalyzed process from Example 1, a 100 gallon glass-lined Pfaudler reactor equipped with overhead stirring, steam heating, and water cooling was charged with deionized water, 136 lbs, and sodium monochloroacetate ("SMCA"), 42 lbs. This was followed by the above amide, 111 lbs. After mixing for about 10 minutes, 20 baume ("Be") hydrochloric acid, 7.1 lbs was added. The reactor content was heated to 120° F., and the pH was monitored to maintain a value of 8.5 to 9.0 via the addition of appropriate amounts of 50% NaOH throughout the course of this quaternization reaction. Once the pH stabilizes without the further addition of any caustic, the reaction is complete. In order to ensure the absence of any SMCA, the pH of the reaction product was raised to 10.2 using 50% NaOH. The temperature was maintained at 85-92° C. for 30-45 minutes to complete the hydrolysis of SMCA. The batch was then cooled to 45° C. and pH adjusted to 4.5-5.5 using 20 Be HCl. The final solids were approximately about 52 wt %. Alternatively, sodium monochloroacetate can be generated in situ using monochloroacetic acid and sodium hydroxide.

For the betaine process in which the amidoamine was formed using sodium methylate catalyzed process, a 100 gallon glass-lined Pfaudler reactor equipped with overhead stirring, steam heating, and water cooling was charged with deionized water, 181 lbs, and SMCA, 29.7 lbs. This was followed by the above amide, 78 lbs. After mixing for about 10 minutes, 20 Be hydrochloric acid, 5.2 lbs was added. The reactor content was heated to 120° F. and the pH was monitored to maintain a value of 8.5 to 9.0 via the addition of appropriate amounts of 50% NaOH throughout the course of this quaternization reaction. Once the pH stabilizes without the further addition of any caustic, the reaction is complete. In order to ensure the absence of any SMCA, the pH of the reaction product was raised to 10.2 using 50% NaOH. The temperature was maintained at 85-92° C. for 30-45 minutes to complete the hydrolysis of SMCA. The batch was then cooled to 45° C. and pH adjusted to 4.5-5.5 using 20 Be HCl. The final solids were about 37 wt %.

The betaines produced in accordance with the foregoing were then diluted with deionized water to reach 35 wt % solids. As shown in Table 3, the beneficial properties were carried over during derivatizations such as the production of betaines.

TABLE 3

Betaine Products

| | Viscosity: Spindle #1 6 rpm, 72 F. | Appearance |
|---|---|---|
| U-Cat (35% solids by moisture balance) | 10.5 cPs | Clear straw colored liquid |
| Sodium Methylate (comparative Ex.) (35% solids by moisture balance) | 16.5 cPs | Clear yellow liquid |

Example 4

Preparation of Sultaines (Prophetic)

In this example, sultaine derivatives are formed using the products of Example 2. In general, epichlorohydrin is reacted with sodium bisulfate (NaHSO₃) to form sodium 3-chloro-2-hydroxypropanesulfonate. This product is then reacted with the alkylamidoalkylamine composition (e.g., from Example 2) to provide the corresponding hydroxysultaine.

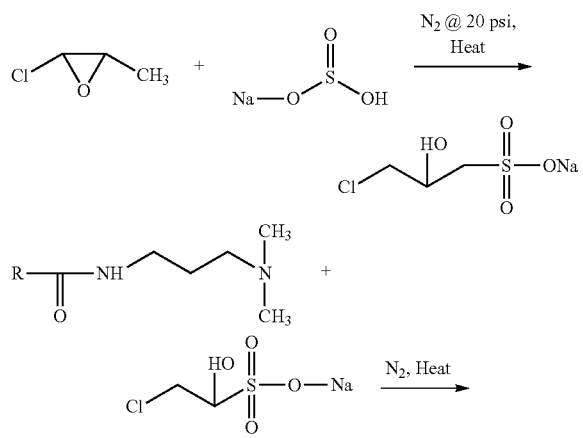

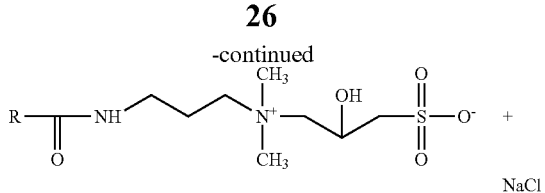

wherein $R^1$ is a saturated or unsaturated, straight or branched chain alkyl having from about 5 to about 25 carbon atoms (preferably about 9 to about 21 carbon atoms, and more preferably still from about 11 to about 17 carbon atoms) and optionally substituted with one or more hydroxyls.

Example 5

Preparation of Phosphitobetaine (Phosphitaines) (Prophetic)

In this example, phosphitobetaine derivatives are formed using the products of Example 2. In general epichlorohydrin is reacted with sodium hydrogen phosphite (NaPO₃H⁻) were reacted to form sodium 3-chloro-2-hydroxypropanephosphinate. This product is then reacted with the alkylamidoalkylamine composition from Example 2 to provide the corresponding phosphitaine (phosphitobetaine). For example, alkylamidopropylhydroxyphosphitaines can be made according to:

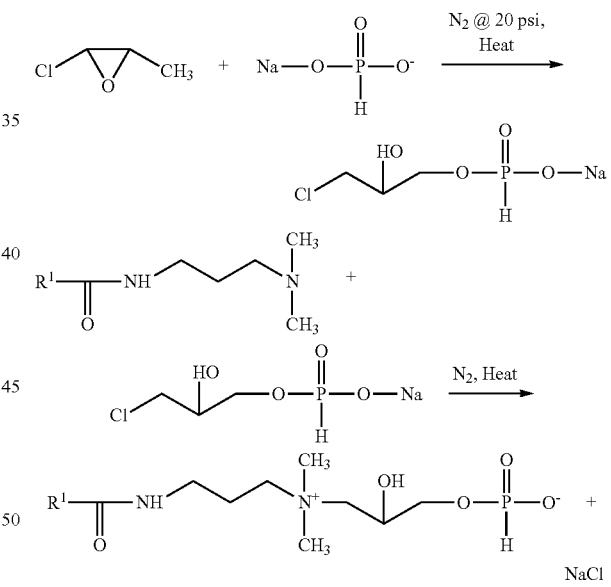

wherein $R^1$ is a saturated or unsaturated, straight or branched chain alkyl having from about 5 to about 25 carbon atoms (preferably about 9 to about 21 carbon atoms, and more preferably still from about 11 to about 17 carbon atoms) and optionally substituted with one or more hydroxyls.

Example 6

Preparation of Amidoamine Oxides (Prophetic)

In this example, the amidoamine composition from Example 2 is oxidized to form the corresponding amidoamine oxide. More specifically, the amidoamine is dispersed in an amount of water that will yield the desired solids in the end product (for example 16 wt %). Then 170 grams of the amidoamine composition is dispersed in 1000 mL of deionized water, and 56.7 grams of 30% hydrogen peroxide is added over a 15 minute period. The mixture is then heated to 70° C., and held for 3 hours at which point the reaction is complete.

Example 7

Preparation of Imidazoline (Prophetic)

In this example, an amidoamine formed from coconut oil and aminoethylethanolamine using the U-Cat of Example 1. The amidoamine composition is loaded into the reactor. The mixture is heated to about 140° C. The pressure is reduced to about 200 mmHg, and then the temperature is increased to about 220° C. at a ramp of about 20° C. per hour. The pressure is then reduced to about 15 mmHg over a period of about 3 hours. At this point, the reaction should be complete and can be analyzed for free diamide to determine completion. Depending on the analyzed amount of diamide, the reaction can be furthered by adding more amine, and the process repeated until a satisfactory diamide content is reached.

It will be appreciated that formation of the imidazoline may be formed using either a one-pot or two-pot process. Preferably, one could proceed directly from the addition of the coconut oil and aminoethylethanolamine to the imidazoline.

From the foregoing, it will be seen that this invention is one well adapted to attain all ends and objectives herein-above set forth, together with the other advantages which are obvious and which are inherent to the invention. Since many possible embodiments may be made of the invention without departing from the scope thereof, it is to be understood that all matters herein set forth are to be interpreted as illustrative, and not in a limiting sense. While specific embodiments have been shown and discussed, various modifications may of course be made, and the invention is not limited to the specific forms or arrangement of parts and steps described herein, except insofar as such limitations are included in the following claims. Further, it will be understood that certain features and subcombinations are of utility and may be employed without reference to other features and subcombinations. This is contemplated by and is within the scope of the claims.

What is claimed and desired to be secured by Letters Patent is as follows:

1. A process for making a fatty amide composition comprising:
    reacting an amine having an active hydrogen and one or more glycerides in the presence of a calcium-containing catalyst to form a fatty amide composition, said calcium-containing catalyst comprising a calcium-containing compound modified with an acid, anhydride, or mixtures thereof, wherein said calcium-containing compound is at least partially dispersed in a dispersing medium, and wherein said catalyst is selected from the group consisting of U-Cat, Catalyst A, Catalyst C, Catalyst Y and Catalyst Z.

2. The process of claim 1 wherein said dispersing medium comprises an alkoxylated alcohol, and said acid is a strong inorganic acid.

3. The process of claim 1 wherein said catalyst is formed by admixing (1) said dispersing medium, wherein said dispersing medium comprises an alkoxylated alcohol or mixtures thereof; (2) said calcium-containing compound that is at least partially dispersible in said dispersing medium, and (3) a carboxylic acid, anhydride, or mixtures thereof having from about 4 to about 15 carbon atoms, with the mole ratio of calcium to said carboxylic acid, anhydride, or mixtures thereof being from about 15:1 to 1:1, to produce a calcium-containing composition; and optionally
    adding an amount of an inorganic acid to neutralize said calcium-containing composition to produce a calcium-containing catalyst.

4. The process of claim 1 wherein said catalyst is formed by admixing (1) said dispersing medium, wherein said dispersing medium consists essentially of media having a boiling point less than about 160° C., (2) said calcium-containing compound that is at least partially dispersible in said dispersing medium, and (3) a carboxylic acid, anhydride, or mixtures thereof having from about 4 to about 15 carbon atoms, with the mole ratio of calcium to said carboxylic acid, anhydride, or mixtures thereof being from about 15:1 to 1:1, to produce a calcium-containing composition.

5. The process according to claim 4 further comprising the step of adding an amount of an inorganic acid, anhydride, or mixtures thereof to produce a partially neutralized calcium-containing catalyst.

6. The process of claim 5 wherein said inorganic acid, anhydride, or mixtures thereof is selected from the group consisting of sulfuric acid, phosphoric acid, oleum, sulfur trioxide, and phosphorous pentoxide, or mixtures thereof.

7. The process of claim 5 further comprising the step of adding a metal alkoxide to the calcium containing composition.

8. The process of claim 5 including heating said partially neutralized catalyst at a temperature of from about 25° C. to about 160° C. under reflux conditions.

9. The process of claim 8 wherein said heating is conducted for a period of 1 to 5 hours.

10. The process of claim 4 wherein said carboxylic acid is selected from the group consisting of octanoic acid, 2-methyl hexanoic acid, heptanoic acid, 3-methyl octanoic acid, 4-ethyl nonanoic acid, 2-ethyl hexanoic acid, or mixtures thereof.

11. The process of claim 1 wherein said dispersing medium consists essentially of one or more branched or straight chain alcohols.

12. The process of claim 11 wherein said branched or straight chain alcohols are selected from the group consisting of methanol, ethanol, 1-propanol, 2-propanol, 2-methyl-2-propanol, 1-butanol, 2,3-dimethyl-1-butanol, 3,3-dimethyl-1-butanol, 2-diethyl-1-butanol, 2-methyl-1-butanol, 3-methyl-1-butanol, 2-butanol, 2-methyl-2-butanol, 2,3-dimethyl-2-butanol, 3,3-dimethyl-2-butanol, 3-methyl-2-butanol, 2-methyl-1-pentanol, 3-methyl-1-pentanol, 4-methyl-1-pentanol, 2-pentanol, 2,4-dimethyl-2-pentanol, 2-methyl-2-pentanol, 3-methyl-2-pentanol, 4-methyl-2-pentanol, 3-pentanol, 2,4,4-trimethyl-2-pentanol, 2,2-dimethyl-3-pentanol, 2,3-dimethyl-3-pentanol, 2,4-dimethyl-3-pentanol, 3-ethyl-3-pentanol, 3-ethyl-2-methyl-3-pentanol, 2-methyl-3-pentanol, 2,3,4-trimethyl-3-pentanol, 1-pentanol, 1-hexanol, 2-hexanol, 2-methyl-2-hexanol, 5-methyl-2-hexanol, 3-hexanol, and 3-methyl-3-hexanol, or mixtures thereof.

13. The process of claim 1 wherein said dispersing medium consists essentially of one or more volatile esters.

14. The process according to claim 13 wherein said volatile ester is an ester of formic acid, acetic acid, propionic acid, butyric acid, or mixtures thereof.

15. The process according to claim 13 wherein said volatile ester is selected from the group consisting of allyl formate, butyl formate, isobutyl formate, sec-butyl formate, ethyl formate, hexyl formate, methyl formate, pentyl formate, isopentyl formate, propyl formate, isopropyl formate, or mixtures thereof.

16. The process according to claim 13 wherein said volatile ester is selected from the group consisting of allyl acetate, butyl acetate, iso-butyl acetate, sec-butyl acetate, tert-butyl acetate, ethyl acetate, methyl acetate, tert-amyl acetate, isopentyl acetate, 2-methyl-3-pentyl acetate, 3-methyl-3-pentyl acetate, 4-methyl-2-pentyl acetate, pentyl acetate, 2-pentyl acetate, 3-pentyl acetate, propyl acetate, isopropyl acetate, 1,2,2-trimethyl propyl acetate, or mixtures thereof.

17. The process of claim 1 wherein said dispersing medium consists essentially of one or more volatile ethers.

18. The process of claim 17 wherein said ether is selected from the group consisting of dimethyl ether, diethyl ether, dimethoxy ethane, diethoxymethane, dibutylether, isopropyl ether, or mixtures thereof.

19. The process of claim 1 wherein said dispersing medium consists essentially of one or more volatile aldehydes and ketones.

20. The process of claim 19 wherein said aldehydes and ketones are selected from the group consisting of acetaldehyde, propionaldehyde, butyraldehyde, hexanal, heptanal, acetone, butanone, pentanones, hexanones, heptanones, or mixtures thereof.

21. The process of claim 4 wherein said dispersing medium consists essentially of media having a boiling point less than 120° C.

22. The process of claim 4 wherein said dispersing medium consists essentially of media having a boiling point between about 80° C. and 140° C.

23. The process of claim 4 further comprising the step of removing the dispersing medium to generate an active catalyst in a solid form.

24. The process of claim 4 wherein said reaction occurs at a temperature greater than about 160° C.

25. The process of claim 4 wherein said glyceride has a boiling point greater than the boiling point of said dispersing medium.

26. The process of claim 4 wherein the glyceride has boiling point about 20° C. or more higher than the boiling point of said dispersing medium.

27. The process of claim 1 wherein said amine is a diamine.

28. The process of claim 27 wherein said amine is defined according to:

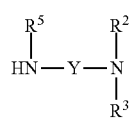

wherein $R^2$ and $R^3$ are independently selected from the group consisting of hydrogen or lower alkyl optionally substituted with one or more hydroxyls or alkoxylated hydroxyls, and at least one of $R^2$ and $R^3$ is not hydrogen;
wherein $R^5$ is hydrogen or lower alkyl; and
wherein Y is alkyl.

29. The process of claim 1 wherein said amine is a monoamine.

30. The process of claim 29 wherein said amine is defined according to:

wherein $R^2$ and $R^3$ are independently selected from the group consisting of hydrogen or lower alkyl optionally substituted with one or more hydroxyls or alkoxylated hydroxyls, and at least one of $R^2$ and $R^3$ is not hydrogen.

31. The process of claim 30 wherein said monoamine is a dialkanolamine or a monoalkanolamine.

32. The process of claim 1 wherein said one or more glyceride is derived from the group consisting of $C_4$ butyric acid (butanoic acid), $C_5$ valeric acid (pentanoic acid), $C_6$ caproic acid (hexanoic acid), 2-ethyl hexanoic acid, $C_7$ enanthic acid (heptanoic acid), $C_8$ caprylic acid (octanoic acid), iso-octanoic acid, $C_9$ pelargonic acid (nonanoic acid), $C_{10}$ capric acid (decanoic acid), $C_{11}$ hendecanoic acid, $C_{12}$ lauric acid (dodecanoic acid), $C_{13}$ tridecanoic acid, isotridecanoic acid, $C_{14}$ myristic acid (tetradecanoic acid), $C_{16}$ palmitic acid (hexadecanoic acid), $C_{17}$ margaric acid (heptadecanoic acid), $C_{18}$ stearic acid (octadecanoic acid), iso-stearic acid, $C_{20}$ arachidic acid (eicosanoic acid), $C_{21}$ heneicosanoic acid, $C_{22}$ behenic acid (docosanoic acid), $C_{24}$ lignoceric acid (tetracosanoic acid), myristoleic acid (14:1), palmiteoleic acid (16:1), petroselinic acid (18:1), ricinoleic acid (18:1), linoleic acid (18:2), linolenic acid (18:3), eleosteric acid (18:3), eoleic acid (18:1), gadoleic acid (20:1), arachidonic acid (20:4), eicosapentaenoic (20:5), eurucic acid (22:1), or combinations thereof.

33. The process of claim 1 wherein said fatty amide comprising said fatty amide composition is a fatty amidoamine defined according to:

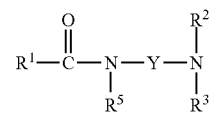

wherein $R^1$ is a saturated or unsaturated, straight or branched chain alkyl having from about 5 to about 25 carbon atoms and optionally substituted with one or more hydroxyls;
wherein $R^2$ and $R^3$ are independently selected from the group consisting of hydrogen or lower alkyl optionally substituted with one or more hydroxyls or alkoxylated hydroxyls, and at least one of $R^2$ and $R^3$ is not hydrogen;
wherein $R^5$ is hydrogen or lower alkyl; and
wherein Y is alkyl.

34. The process of claim 33 wherein said fatty amidoamine is a $C_{12}$ to $C_{18}$ fatty amidoamine.

35. The process of claim 34 wherein said fatty amidoamine is cocoamidopropyldialkylamine.

36. The process of claim 1 wherein said fatty amide comprising said fatty amide composition is defined according to:

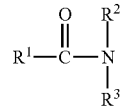

wherein R¹ is a saturated or unsaturated, straight or branched chain alkyl having from about 5 to about 25 carbon atoms and optionally substituted with one or more hydroxyls; and wherein R² and R³ are independently selected from the group consisting of hydrogen or lower alkyl optionally substituted with one or more hydroxyls or alkoxylated hydroxyls, and at least one of R² and R³ is not hydrogen.

37. The process of claim 1 wherein said fatty amide comprising said fatty amide composition is a fatty amidoamine oxide defined according to:

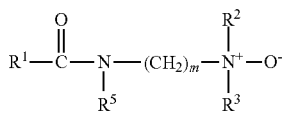

wherein R¹ is a saturated or unsaturated, straight or branched chain alkyl having from about 5 to about 25 carbon atoms and optionally substituted with one or more hydroxyls;

wherein R² and R³ are independently selected from the group consisting of hydrogen or lower alkyl optionally substituted with one or more hydroxyls or alkoxylated hydroxyls, and at least one of R² and R³ is not hydrogen;

wherein R⁵ is hydrogen or lower alkyl; and wherein m is 1, 2, 3, 4, 5, or 6.

38. The process of claim 1 wherein said fatty amide comprising said fatty amide composition is a quaternized fatty amidoamine defined according to:

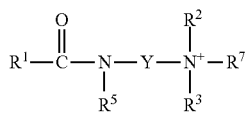

wherein R¹ is a saturated or unsaturated, straight or branched chain alkyl having from about 5 to about 25 carbon atoms and optionally substituted with one or more hydroxyls;

wherein R² and R³ are independently selected from the group consisting of hydrogen or lower alkyl optionally substituted with one or more hydroxyls or alkoxylated hydroxyls and at least one of R² and R³ is not hydrogen;

wherein R⁵ is hydrogen or alkyl;

wherein Y is alkyl; and wherein R⁷ is alkyl or aralkyl optionally containing a hydroxy or alkoxy.

39. A process for forming a fatty imidazoline comprising:

the process of claim 1, wherein the fatty amide composition comprises a fatty amidoamine composition defined according to:

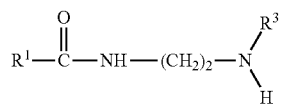

and further comprising cyclizing the fatty amidoamine to form the fatty imidazoline;

wherein said imidazoline is defined according to:

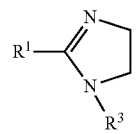

wherein R¹ is a saturated or unsaturated, straight or branched chain alkyl having from about 5 to about 25 carbon atoms and optionally substituted with one or more hydroxyls; and wherein R³ is selected from the group consisting of hydrogen or lower alkyl optionally substituted with one or more hydroxyls or alkoxylated hydroxyls.

40. The process of claim 39 wherein R³ is —CH₂CH₂OH or —CH₂CH₂OCH₂CH₂OH.

41. The process of claim 39 wherein said imidazoline is quaternized with a quaternizing agent having the formula R⁷X to form a compound according to:

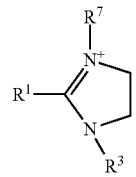

wherein R¹ is a saturated or unsaturated, straight or branched chain alkyl having from about 5 to about 25 carbon atoms and optionally substituted with one or more hydroxyls;

wherein R² and R³ are independently selected from the group consisting of hydrogen or lower alkyl optionally substituted with one or more hydroxyls or alkoxylated hydroxyls, and at least one of R² and R³ is not hydrogen;

wherein R⁵ is hydrogen or alkyl; and wherein m is 1, 2, 3, 4, 5, or 6;

wherein R⁷ is alkyl or aralkyl optionally containing a hydroxy or alkoxy; and wherein X is a leaving group.

42. A process for making a composition comprising an amphoteric compound, comprising:

the process of claim 33; and further comprising:

reacting the fatty amidoamine composition prepared by the process of claim 34 with a haloalkylanionic salt, cyclic sulfonate, or cyclic sulfate, and wherein the amphoteric compound is selected from the group consisting of betaines, sulfobetaines, sulfitobetaines, sulfatobetaines, phosphinate betaines, phosphonate betaines, phosphitobetaines, and phosphatobetaines.

43. The process of claim 42 wherein said amphoteric compound is defined according to:

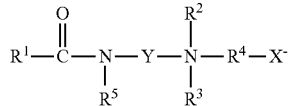

wherein R¹ is a saturated or unsaturated, straight or branched chain alkyl having from about 5 to about 25 carbon atoms and optionally substituted with one or more hydroxyls;

wherein R² and R³ are independently selected from the group consisting of hydrogen or lower alkyl optionally substituted with one or more hydroxyls or alkoxylated hydroxyls, and at least one of R² and R³ is not hydrogen;
wherein R⁴ is selected from the group consisting of saturated or unsaturated, straight or branched chain lower alkyl, optionally substituted with one or more hydroxyls; and
wherein X⁻ is selected from the group consisting of —CO₂⁻, —SO₂O⁻, —OSO₂⁻, —OSO₃⁻, —PR⁶O₂⁻, —P(OR⁶)O₂⁻, —OP(O)(H)O⁻), and —OP(O)(OH)O⁻, and wherein R⁶ is hydrogen or lower alkyl;
wherein R⁵ is hydrogen or lower alkyl; and
wherein Y is alkyl.

44. The process of claim 42 wherein said haloalkylanionic salt is a haloalkylcarboxylate salt and said amphoteric compound is a betaine defined according to:

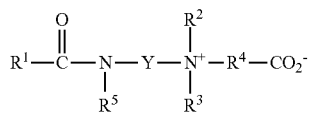

wherein R¹ is a saturated or unsaturated, straight or branched chain alkyl having from about 5 to about 25 carbon atoms and optionally substituted with one or more hydroxyls;
wherein R² and R³ are independently selected from the group consisting of hydrogen or lower alkyl optionally substituted with one or more hydroxyls or alkoxylated hydroxyls, and at least one of R² and R³ is not hydrogen;
wherein R⁴ is selected from the group consisting of saturated or unsaturated, straight or branched chain lower alkyl, optionally substituted with one or more hydroxyls;
wherein R⁵ is hydrogen or lower alkyl; and
wherein Y is alkyl.

45. The process of claim 44 wherein said amphoteric compound is an alkylamidopropylbetaine defined according to:

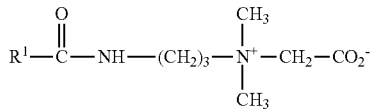

wherein R¹ is a saturated or unsaturated, straight or branched chain alkyl having from about 5 to about 25 carbon atoms and optionally substituted with one or more hydroxyls.

46. The process of claim 42 wherein said haloalkylanionic salt is a haloalkylsulfonate salt or sultone and said amphoteric compound is a sultaine defined according to:

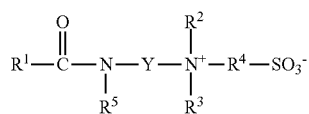

wherein R¹ is a saturated or unsaturated, straight or branched chain alkyl having from about 5 to about 25 carbon atoms and optionally substituted with one or more hydroxyls;

wherein R² and R³ are independently selected from the group consisting of hydrogen or lower alkyl optionally substituted with one or more hydroxyls or alkoxylated hydroxyls, and at least one of R² and R³ is not hydrogen;
wherein R⁴ is selected from the group consisting of saturated or unsaturated, straight or branched chain lower alkyl, optionally substituted with one or more hydroxyls;
wherein R⁵ is hydrogen or lower alkyl; and
wherein Y is alkyl.

47. The process of claim 46 wherein said sultaine is one defined according to:

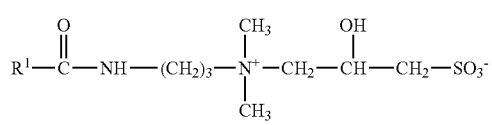

wherein R¹ is a saturated or unsaturated, straight or branched chain alkyl having from about 5 to about 25 carbon atoms and optionally substituted with one or more hydroxyls.

48. The process of claim 42 wherein said haloalkylanionic salt is a haloalkylsulfite salt and said amphoteric compound is a sulfitobetaine defined according to:

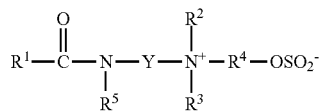

wherein R¹ is a saturated or unsaturated, straight or branched chain alkyl having from about 5 to about 25 carbon atoms and optionally substituted with one or more hydroxyls;
wherein R² and R³ are independently selected from the group consisting of hydrogen or lower alkyl optionally substituted with one or more hydroxyls or alkoxylated hydroxyls, and at least one of R² and R³ is not hydrogen;
wherein R⁴ is selected from the group consisting of saturated or unsaturated, straight or branched chain lower alkyl, optionally substituted with hydroxyl;
wherein R⁵ is hydrogen or lower alkyl; and
wherein Y is alkyl.

49. The process of claim 48 wherein said sulfitobetaine is one defined according to:

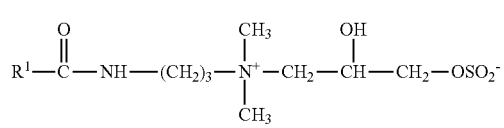

wherein R¹ is a saturated or unsaturated, straight or branched chain alkyl having from about 5 to about 25 carbon atoms and optionally substituted with one or more hydroxyls.

50. The process of claim 42 wherein said haloalkylanionic salt is a haloalkylsulfate salt or cyclic sulfate and said amphoteric compound is a sulfatobetaine defined according to:

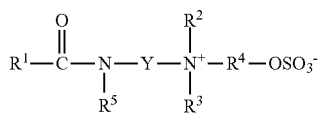

wherein R¹ is a saturated or unsaturated, straight or branched chain alkyl having from about 5 to about 25 carbon atoms and optionally substituted with one or more hydroxyls;

wherein R² and R³ are independently selected from the group consisting of hydrogen or lower alkyl optionally substituted with one or more hydroxyls or alkoxylated hydroxyls, and at least one of R² and R³ is not hydrogen;

wherein R⁴ is selected from the group consisting of saturated or unsaturated, straight or branched chain lower alkyl, optionally substituted with hydroxyl;

wherein R⁵ is hydrogen or lower alkyl; and wherein Y is alkyl.

51. The process of claim 20 wherein said sulfatobetaine is one defined according to:

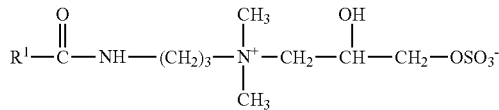

wherein R¹ is a saturated or unsaturated, straight or branched chain alkyl having from about 5 to about 25 carbon atoms and optionally substituted with one or more hydroxyls.

52. The process of claim 42 wherein said haloalkylanionic salt is a haloalkylphosphinate salt and said amphoteric compound is a phosphinate betaine defined according to:

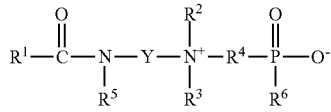

wherein R¹ is a saturated or unsaturated, straight or branched chain alkyl having from about 5 to about 25 carbon atoms and optionally substituted with one or more hydroxyls;

wherein R² and R³ are independently selected from the group consisting of hydrogen or lower alkyl optionally substituted with one or more hydroxyls or alkoxylated hydroxyls, and at least one of R² and R³ is not hydrogen;

wherein R⁴ is selected from the group consisting of saturated or unsaturated, straight or branched chain lower alkyl, optionally substituted with hydroxyl;

wherein R⁵ is hydrogen or lower alkyl;

wherein R⁶ is hydrogen or lower alkyl; and wherein Y is alkyl.

53. The process of claim 52 wherein said phosphinate betaine is one defined according to:

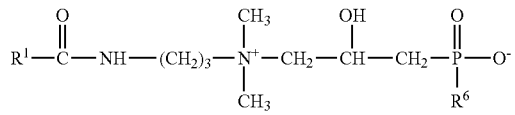

wherein R¹ is a saturated or unsaturated, straight or branched chain alkyl having from about 5 to about 25 carbon atoms and optionally substituted with one or more hydroxyls; and wherein R⁶ is hydrogen or lower alkyl.

54. The process of claim 42 wherein said haloalkylanionic salt is a haloalkylphosphonate salt and said amphoteric compound is a phosphonate betaine defined according to:

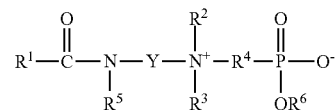

wherein R¹ is a saturated or unsaturated, straight or branched chain alkyl having from about 5 to about 25 carbon atoms and optionally substituted with one or more hydroxyls;

wherein R² and R³ are independently selected from the group consisting of hydrogen or lower alkyl optionally substituted with one or more hydroxyls or alkoxylated hydroxyls, and at least one of R² and R³ is not hydrogen;

wherein R⁴ is selected from the group consisting of saturated or unsaturated, straight or branched chain lower alkyl, optionally substituted with hydroxyl;

wherein R⁵ is hydrogen or lower alkyl;

wherein R⁶ is hydrogen or lower alkyl; and wherein Y is alkyl.

55. The process of claim 54 wherein said phosphonate betaine is one defined according to:

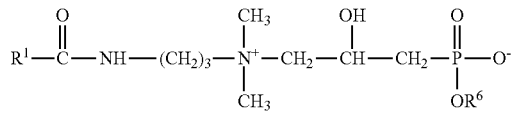

wherein R¹ is a saturated or unsaturated, straight or branched chain alkyl having from about 5 to about 25 carbon atoms and optionally substituted with one or more hydroxyls; and wherein R⁶ is hydrogen or lower alkyl.

56. The process of claim 42 wherein said haloalkylanionic salt is a haloalkylphosphite salt and said amphoteric compound is a phosphitobetaine defined according to:

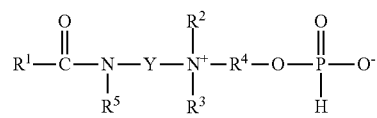

wherein R¹ is a saturated or unsaturated, straight or branched chain alkyl having from about 5 to about 25 carbon atoms and optionally substituted with one or more hydroxyls;

wherein R² and R³ are independently selected from the group consisting of hydrogen or lower alkyl optionally substituted with one or more hydroxyls or alkoxylated hydroxyls, and at least one of $R^2$ and $R^3$ is not hydrogen;

wherein $R^4$ is selected from the group consisting of saturated or unsaturated, straight or branched chain lower alkyl, optionally substituted with hydroxyl;

wherein $R^5$ is hydrogen or lower alkyl; and wherein Y is alkyl.

57. The process of claim 56 wherein said phosphitobetaine is one defined according to:

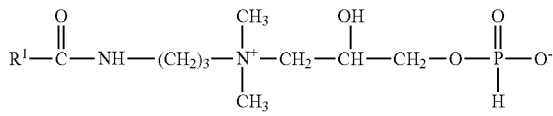

wherein $R^1$ is a saturated or unsaturated, straight or branched chain alkyl having from about 5 to about 25 carbon atoms and optionally substituted with one or more hydroxyls.

58. The process of claim 42 wherein said haloalkylanionic salt is a haloalkylphosphate salt and said amphoteric compound is a phosphatobetaine defined according to:

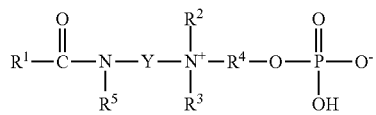

wherein $R^1$ is a saturated or unsaturated, straight or branched chain alkyl having from about 5 to about 25 carbon atoms and optionally substituted with one or more hydroxyls;

wherein $R^2$ and $R^3$ are independently selected from the group consisting of hydrogen or lower alkyl optionally substituted with one or more hydroxyls or alkoxylated hydroxyls, and at least one of $R^2$ and $R^3$ is not hydrogen;

wherein $R^4$ is selected from the group consisting of saturated or unsaturated, straight or branched chain lower alkyl, optionally substituted with hydroxyl;

wherein $R^5$ is hydrogen or lower alkyl; and wherein Y is alkyl.

59. The process of claim 58 wherein said phosphatobetaine is one defined according to:

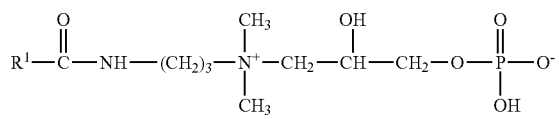

wherein $R^1$ is a saturated or unsaturated, straight or branched chain alkyl having from about 5 to about 25 carbon atoms and optionally substituted with one or more hydroxyls.

* * * * *